United States Patent [19]

Margolin

[11] Patent Number: 5,962,478
[45] Date of Patent: Oct. 5, 1999

[54] INHIBITION OF TUMOR NECROSIS FACTOR α

[76] Inventor: Solomon B. Margolin, 6723 Desco Dr., Dallas, Tex. 75225

[21] Appl. No.: 09/044,441

[22] Filed: Mar. 19, 1998

Related U.S. Application Data

[63] Continuation-in-part of application No. PCT/US96/14926, Sep. 17, 1996
[60] Provisional application No. 60/003,955, Sep. 19, 1995.
[51] Int. Cl.$^6$ ...................................................... A61K 31/44
[52] U.S. Cl. ........................... 514/345; 514/311; 514/334
[58] Field of Search ................................ 514/311, 345, 514/334

[56] References Cited

U.S. PATENT DOCUMENTS

| | | | |
|---|---|---|---|
| 3,839,346 | 10/1974 | Gadekar | 260/297 |
| 3,974,281 | 8/1976 | Gardekar | 424/263 |
| 4,042,699 | 8/1977 | Gardekar | 424/263 |
| 5,310,562 | 5/1994 | Margolin | 424/489 |
| 5,518,729 | 5/1996 | Margolin | 424/423 |
| 5,641,751 | 6/1997 | Heavner | 514/13 |
| 5,716,632 | 2/1998 | Margolin | 424/423 |

*Primary Examiner*—James H. Reamer
*Attorney, Agent, or Firm*—John H. Crozier

[57] ABSTRACT

In a preferred embodiment, a method for the inhibition of the synthesis and release of tumor necrosis factor from various cells, comprising: administering to a human or other mammal an effective dose of one or more pharmaceutical substances selected from the group consisting of N-substituted 2(1H)pyridones, N-substituted 3(1H)pyridones, and pharmaceutically acceptable salts thereof.

8 Claims, 9 Drawing Sheets

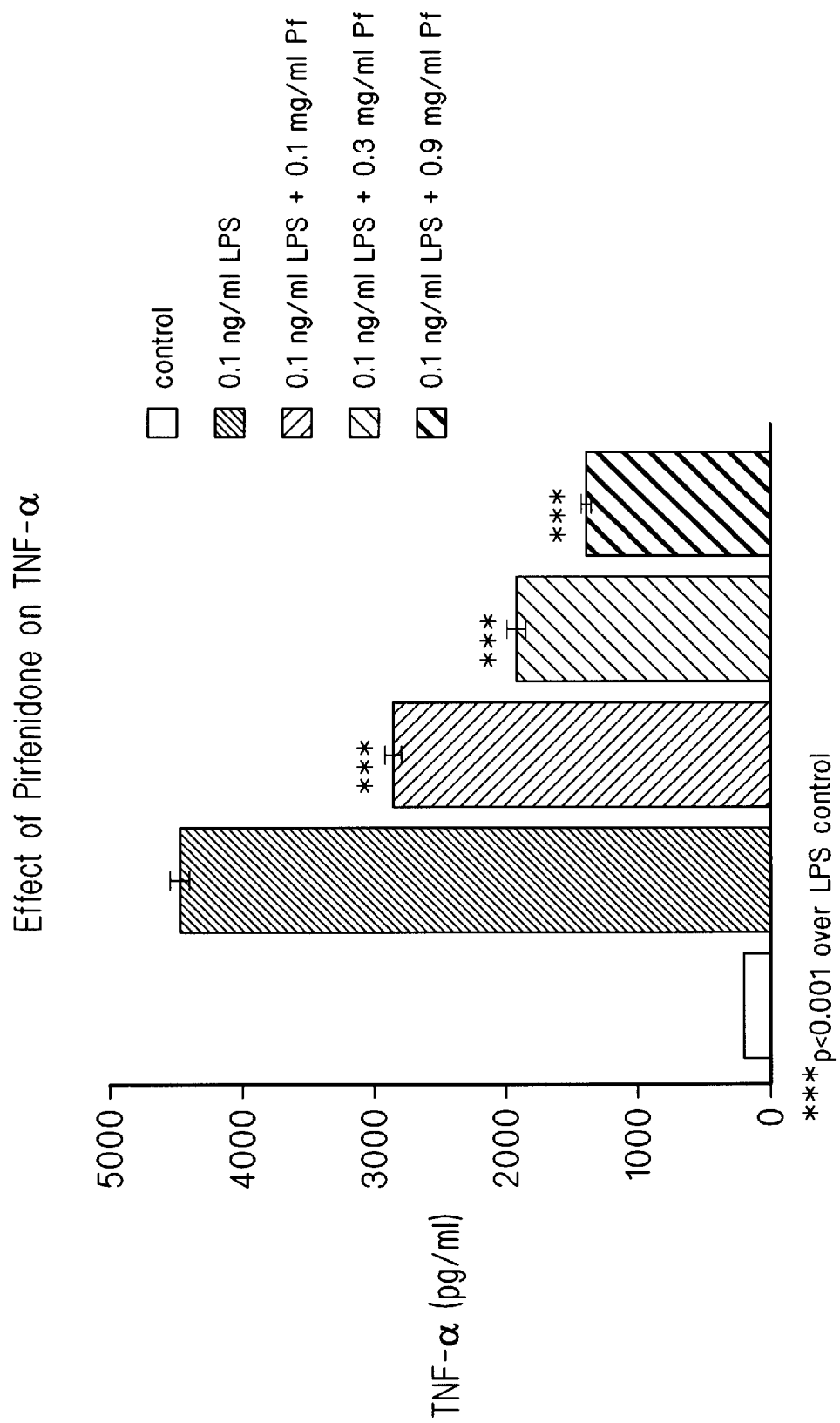

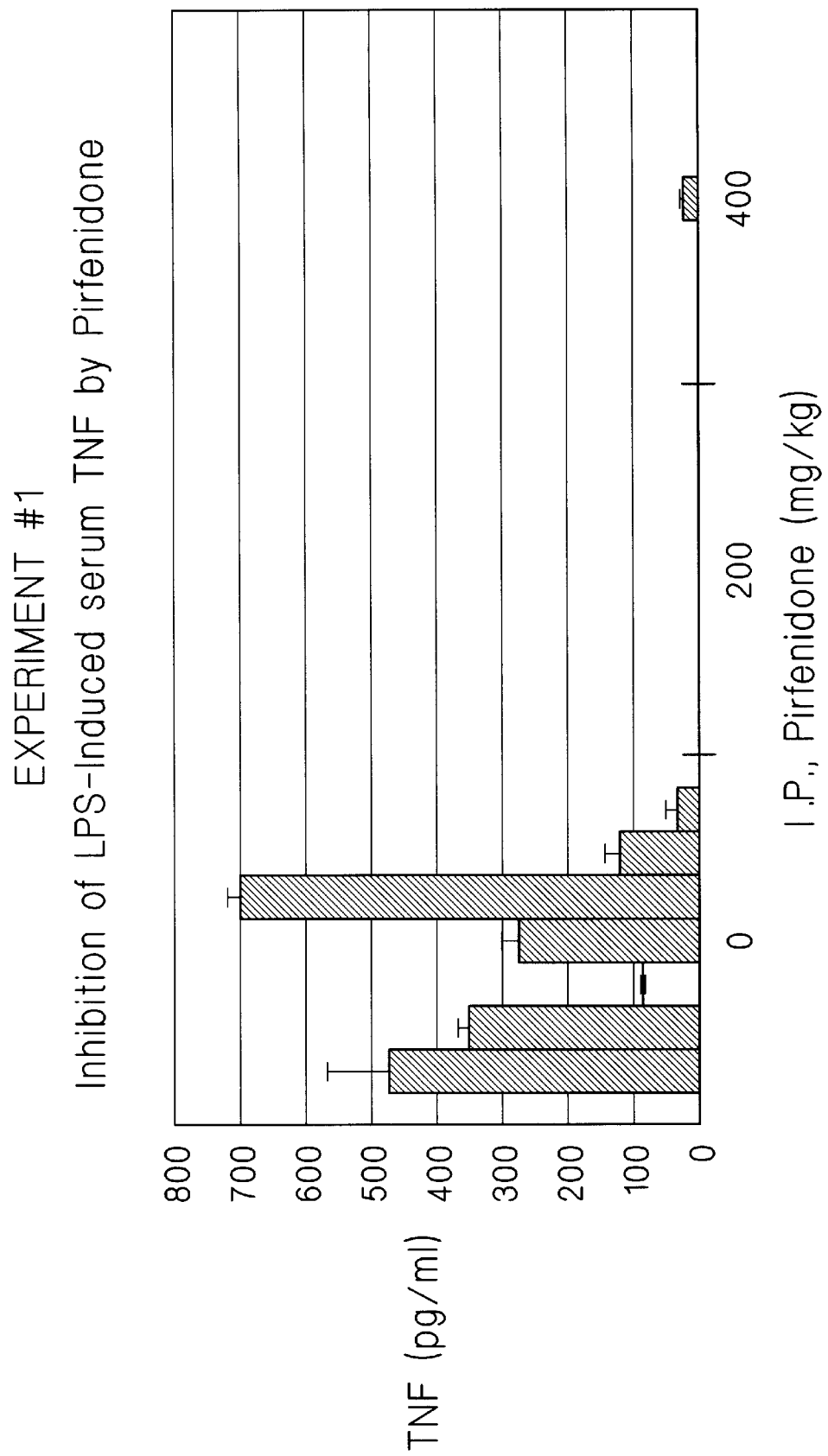

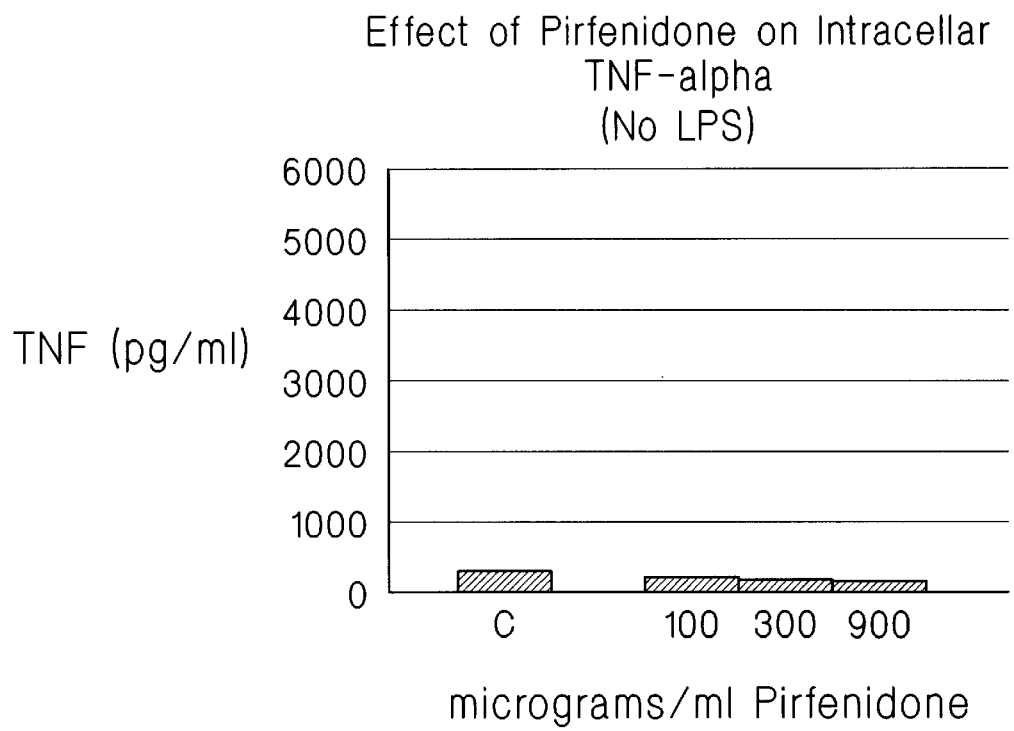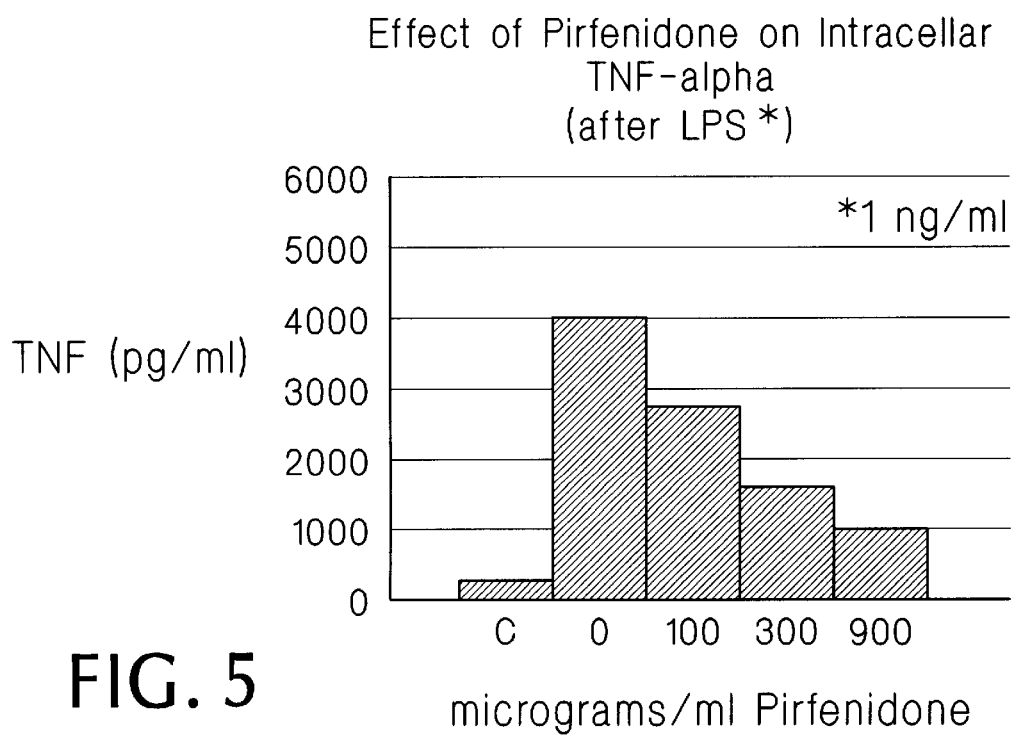
FIG. 5

INHIBITION OF TUMOR NECROSIS FACTOR α

CROSS-REFERENCE TO RELATED APPLICATIONS

The present application is a continuation-in-part of PCT/US96/14926, filed Sep. 17, 1996. Benefit is claimed of U.S. Provisional Application Ser. No. 60/003,955, filed Sep. 19, 1995.

BACKGROUND OF THE INVENTION

1. Field of the Invention

The present invention relates to pharmaceutical compositions and, more particularly, but not by way of limitation, to novel compositions and methods for inhibition of pathophysiologic effects of excessive amounts of TNF-α in the blood, tissues, or organs of mammals including humans.

2. Background Art

Current evidence indicates that seemingly diverse immune-mediated diseases involve similar pathogenic mechanisms, and a growing number of key effector molecules known as cytokines. A biochemical cascade of pathophysiologic events is triggered by excessive tissue or blood concentrations of TNF-α released or synthesized following cellular, tissue, or organ injury. TNF-α plays a prominent role in immune and host defense response. There is strong evidence that abnormally high production and release from cells of TNF-α contributes to disease initiation and progression in rheumatoid arthritis, systemic inflammatory syndromes, diabetes, multiple sclerosis, and many other immune-mediated disorders (L. Propert, J. Leukocyte Biol., 59:518–525, 1996).

In every one of these conditions, the initiating and sustaining pathophysiologic action is directly a result of an immediate local release and synthesis of massive amounts of TNF-α from several types of cells at or adjacent to the injury site. The locally released TNF-α is followed by additional synthesis and release of TNF-α by invading macrophages drawn to the injury site by a cascade of chemotactic cytokines released locally from cells in response to the greatly elevated TNF-α concentrations.

TNF-α is a 17 kDa, multi-functional peptide produced by a wide variety of cells during host responses to tissue or organ injury including microbial infections and neoplastic diseases. Activated macrophages are a major cellular source for TNF-α, although other cell types such as T-cells, mast cells, neutrophils, endothelial cells, microglia, and astrocytes can be stimulated to secrete TNF-α. TNF-α also plays an important role in the initiation of inflammation and the pathophysiologic consequences that result from this process.

There are several disease states in which excessive or unregulated TNF-alpha production by monocytes, macrophages or related cells are implicated in exacerbating and/or causing the disease. These include endotoxemia (sepsis), toxic shock syndrome (Tracey et al., Nature, 330:662–64, 1987; Basger et al., Circ. Shock. 27:51–61, 1989, and Hinshaw et al., 30:279–292, 1990); cachexia (Dezube et al., Lancet, 335 [8690]:662, 1990); Adult Respiratory Distress Syndrome (ARDS) where TNF-α concentrations in excess of 12,000 pg per ml have been detected in pulmonary aspirates from ARDS patients (Millar et al., Lancet, [8665] 2, 712–714. Systemic infusion of recombinant TNF-alpha resulted in changes typically seen in ARDS (Ferrai-Baliviera et al., Arch. Surgery, 124:1400–1405, 1989.) TNF-α is widely expressed in monocytes, macrophages, lymphocytes, natural killer cells, endothelial cells, mast cells, neutrophils and eosinophils, glial cells and astrocytes, smooth muscle cells and certain tumor cells. TNF-α can be produced mainly by lymphocytes, astrocytes, lymphokine-activated killer cells and myeloma cells. Overproduction of TNF-α and/or β is closely linked to development of many diseases, including septic shock, adult respiratory distress syndrome, rheumatoid arthritis, selective autoimmune disorders, graft-host disease following bone marrow transplantation and cachexia. Other diseases associated with excessive TNF-production include: hemorrhagic shock, asthma and post-renal dialysis syndrome. The multiplicity of actions of TNF-α and -β can be ascribed to the facts that TNF-α and -62 actions result in activation of multiple signal transduction pathways, kinases, transcription factors, as well as an unusually large array of cellular genes. (Walajtys-Rode, Elizbieta, Kosmos (Warsaw), 44, 451–464, 1995, C.A. 124:199735a, 1995).

TNF-α exhibits a plethora of other functions such as induction of IL1, stimulation of neutrophil degranulation, and enhancement of phagocytosis. Endotoxin from gram negative bacteria has been used to induce TNF-α both in vivo and in vitro. In addition to endotoxin, certain microorganisms as well as other substances, such as IL1, are capable of inducing secretion of TNF-α from stimulated peritoneal macrophages. (H. J. Wanebo, "Tumor Necrosis Factors," Seminars in Surgical Oncology, 1989, 5:402–413.)

Thus, TNF-α is a potent immunomediator and proinflammatory cytokine that has been implicated in the pathogenesis of a large number of human diseases. The location of its gene within the major histocompatability complex and biological activities have raised the possibility that polymorphism within this locus may contribute to the genetic association of this region of the genome with a wide range of autoimmune and infectious diseases.

TNF-α inhibitors can be useful in the therapeutic or prophylactic treatment of a variety of allergic and traumatic disorders including asthma, chronic bronchitis, many skin disorders (including atopic dermatitis and urticaria), allergic rhinitis, allergic conjunctivitis, vernal conjunctivitis, eosinophilic granuloma, psoriasis, reperfusion injury of the myocardium or brain, cystic fibrosis, chronic glomerulonephritis, and adult respiratory distress syndrome (ARDS). The principal cytokine that mediates the complex processes triggered by injury to a cell or tissue is TNF-α which elicits complex biological responses from virtually every type of cell that it binds. (Jour. Cardiovas. Pharm., 25(S1–S8, 1995).

TNF-α antagonists can be very effective in the treatment of disorders which follow cellular, tissue or organ injury, and may be as effective, or even more potent, than corticosteroids or immunosuppressants without producing the side effects common to these agents.

Characterization of TNF-

TNF-α is widely expressed in monocytes, macrophages, lymphocytes, natural killer cells, endothelial cells, mast cells, neutrophils and eosinophils, glial cells, and astrocytes, smooth muscle cells and certain tumor cells. TNF-α can be produced mainly by lymphocytes, astrocytes, lymphokine-activated killer cells, and myeloma cells. TNF-α and TNF-β bind to the very same cell surface receptors, and are functionally similar, and almost identical in chemical structure (E. Walajytys-Rode. Kosmos [Warsaw], 44:451–64, 1995; C.A. 124:199735a, 1996).

TNF-α is among the cytokines that are produced and stored by most types of cells in various mammalian organs and tissues. Although first described as a product released from activated macrophages that lysed selected tumor cell lines, TNF-α is now recognized as a versatile and ubiquitous cytokine. TNF-α effects on cells depends on both its concentration at the tissue or organ site, and the embryological lineage of the target cells.

TNF-α has been demonstrated to orchestrate its pro-inflammatory effects in response to injury by regulating the cascade and compartmentalized release of secondary messenger cytokines and non-cytokine signaling biochemicals. TNF-α is not limited to regulation of cell growth, but also has remarkable effects on cellular functions. Although pathophysiological effects of TNF-α are generally limited to situations in which TNF-α levels are excessively high (such as occurs during gram-negative infections, allergic reactions, thermal burns, neoplasia and radiation or traumatic injury), TNF-α mRNA and protein are readily identified in the absence of tissue injury, inflammation or neoplasia. On the other hand, very low levels of TNF-α mRNA and protein are readily identified in the absence of cell or tissue injury, indicating that TNF-α can serve, in concert with other regulatory agents, as a normal mediator of cell and tissue homeostasis (Terranova et al., *PSEBM*, 209:325, 1995).

TNF-α (along with its pharmacologic twin, TNF-β, and first cousin, IL1β) remains the master driving force in implementing the cascade of pathobiologic processes, both physiological and biochemical, which directly and indirectly trigger untoward clinical manifestations of a very broad spectrum of human diseases and disorders. These acute and chronically harmful actions, caused by injuries of diverse etiology, not only are manifest upon clinical examination, but are also revealed by (1) measurable flagrant, often life threatening, organ dysfunction, and (2) appropriate pathophysiologic examination of representative tissues and cells taken from the dysfunctional organs.

As expressed in *Annals of Internal Medicine*, Vol. 115; 464, 1993, TNF-α:

(1) Stimulates release of interleukin-1, interleukin-6, interleukin-8, platelet-activating factor, leukotrienes, thromboxane A2, prostanglandins; may be able to stimulate macrophages directly to promote its own release.

(2) Has only a weak effect on T cells.

(3) Stimulates production of polymorphonucelear cells by bone marrow and enhances their phagocytic activity.

(4) Promotes adhesion of endothelial cells, polymorphonuclear cells, eosinophils, basophils, monocytes, and occasionally, lymphocytes by inducing increased expression of adhesion molecules.

(5) Activates common pathway of coagulation and complement system.

(6) Is directly toxic to vascular endothelial cells; increasing microvascular permeability.

(7) Produces a dose-dependent increase in endothelial procoagulant activity; may inhibit thrombomodulin expression at endothelial cell surface.

(8) Suppresses lipoprotein lipase activity; inhibits acetate formation by adipocytes; decreased incorporation of glucose into cells.

(9) Stimulates collagenase release; has variable effects on fibroblast growth, depending on the presence of other mediators.

(10) Reduces transmembrane potential of muscle cells and myocyte shortening.

(11) Induces class I histocompatability molecules.

(12) Acts directly on hypothalamus to produce fever.

The discovery of compounds which inhibit TNF-α overproduction and release will provide a therapeutic approach for those diseases in which excessive or unregulated TNF-α tissue levels is implicated, and also contribute to the understanding of how this molecule is synthesized, processed, secreted and metabolized.

Authors describe TNF-α mediated pathologies such as infectious disease and shock, inflammatory bowel disease, and rheumatoid arthritis, and the use of anti-TNF-α monoclonal antibodies in TNF-α blockade (M. W. Bodner and R. Foulkes, "Therap. Modulation Cytokines," 1996, 221–236 Ed. B. Henderson; B. Bodner, CRC:Boca Raton, Fla.).

TNF-α inhibitors are useful in the treatment of a variety of allergic, traumatic and other injurious disorders including: asthma, chronic bronchitis, atopic dermatitis, urticaria, allergic rhinitis, allergic conjunctivitis, eosiniophilic granuloma, rheumatoid arthritis, septic shock, ulcerative colitis, Crohn's disease, reperfusion injury of the myocardium and brain, chronic glomerulonephritis, and adult respiratory distress syndrome (ARDS).

TNF-α, a pleiotropic cytokine, is produced, stored or released by macrophages and other cells as an initial response when exposed to a variety of infections or non-infectious disorders. TNF-α is now known to be involved in immunological reactions as well. In addition, excessively high blood or tissue levels of TNF-α are often lethal to cells, tissues, organs, as well as the host, (Tracey and Cerami, *PSEBM* 206:233–240, 1992).

TNF-α is secreted by monocytes, macrophages, T-cells, natural killer cells, mast cells, neutrophils, fibroblasts and many other types of cells, in response to stimulation by lipo-polysaccharides (LPS), viruses, bacteria, parasites, antigens and allograft rejection or other injury.

TNF-α also can cause changes in the rate of production and secretion of collagenase, collagen, fibronectin, and glycosaminoglycoside (Duncan and Berman, *Jour. Invest. Derm.*, 92:699–706, 1989; E. J. Ziegler, *N.E. Jour. Med.*, 318:1533, 1988; R. C. Bond, *Ann. Intern. Med.*, 115:457–469, 1991; B. Beutler, *Hosp. Prac.*, pgs. 45–52, Apr. 15, 1993; *Nature* (London), 316:552–554 (1985).

The production and release of TNF-α at sites of injury directly or indirectly recruits additional macrophages to the site, and activates macrophages already present. TNF-α also has been shown to be chemotactic for monocytes. TNF-α also activates macrophages and enhances their cytotoxic potential in vitro.

Since TNF-α is an important mediator of many reactive pathophysiologic states or diseases, inhibitors of TNF-α production can have utility in any pathophysiologic state or disease in which abnormally high levels of TNF-α are present. The compounds of this invention inhibit or block the (1) overproduction and release of TNF-α, and (2) pharmacologically inhibit or block the untoward toxic or lethal effects of high levels of TNF-α.

Excessive TNF-α tissue levels have been implicated in mediating or exacerbating a number of diseases including: rheumatoid arthritis, rheumatoid spondylitis, osteoarthritis, gouty arthritis and other arthritic conditions; also general sepsis, gram-negative sepsis, septic-shock, endotoxic shock, toxic shock syndrome, adult respiratory distress syndrome (ARDS), cerebral malaria, chronic pulmonary inflammatory disease, silicosis, asbestosis, pulmonary sarcoidosis, bone resorption diseases, graft vs. host reactions, allograft rejections; also fever and myalgias due to bacterial or viral infections, such as influenza; cachexia secondary to acquired immune deficiency syndrome (AIDS), keloid formation, scar tissue formation, Crohns disease, ulcerative colitis, or pyresis; a number of "autoimmune diseases" such as multiple sclerosis, autoimmune diabetes, and systemic lupus erythematosus. (Tracey et al., *Nature,* 330:662–664, 1987; Badger et al., *Circ. Shock.,* 27:51–61, 1989 and Hinshaw et al., *Circ. Shock.,* 30:279–292, 1990; cachexia (Dezube et al., Lancet, 335(8690): 662,1990).

The phrase "TNF-α mediated disease or disease states" means, all diseases states in which TNF-α plays a direct role, either by excessive production or release of TNF-α, itself, or by TNF-α causing production or release of another pathophysiological biochemical agent, or cytokine.

"Cytokine" means any secreted polypeptide that affects the functions of cells, and is a molecule which modulates interactions between cells in response to untoward exposure (for example, injury of various types including an allergic reaction).

The term "inhibiting the overproduction and/or release of TNF-α" means:

a) decrease of excessive in vivo TNF-α levels, respectively, in an animal or human to normal levels for several types of cells, including but not limited to monocytes or macrophages;

b) a down regulation in a human tissue of excessive, in vitro or in-vivo TNF-α levels, respectively to normal levels; or c) a down regulation, by inhibition of the direct synthesis of TNF-α levels as a post-translation event.

The term "prevention of the pathophysiologic effects of excessively high levels of TNF-α in tissues and organs means the pharmacologic inhibition of the untoward, toxic or lethal effects of excessively high tissue levels of TNF-α.

Disorders of the Central Nervous System (Injuries and Damage to the Central Nervous System)

The expression of various cytokines or their genes is altered in the brain in a variety of CNS diseases such as multiple sclerosis, acquired immunodeficiency syndrome (AIDS) encephalitis, Alzheimer's disease, scrapie, and viral or bacterial infection. Production of cytokines within the CNS may arise from multiple sources including infiltrating mononuclear cells such as T cells and macrophages and also from resident neural cells, particularly the astrocytes and microglia. The glial cells produce a variety of cytokines, including IL1, TNF-α, and TNF-β, as part of a CNS-cytokine network.

Astrocytes, the most abundant glial cells in the CNS, produce TNF-α in response to a variety of stimuli, including LPS, the cytokines Il-1B and IFN-ψ, and Newcastle's disease virus (NDV) (Chung, I. Y. and E. N. Benveniste, *J. Immunol.,* 144:2999, 1990, A. P. Lieberman et al., *Proc. Natl. Acad. Sci.,* U.S.A. 66:634B, 1989).

Whether in diseases where they are expressed, such as AIDS encephalitis, Alzheimer's disease, or multiple sclerosis, cytokines often are neuropathogenic mediators, and afford possibilities for therapeutic intervention (I. L. Campel et al., *Ann. N.Y. Acad. of Sciences,* 771: 301, 1995).

Effect of TNF-α on Cells of the Central Nervous System

Babak Arvin et al., (*Ann. N.Y. Acad. Sciences,* 765: 62–71, 1995) reviewed evidence for CNS production of TNF-α, involvement of TNF-α in brain injury, the role of PMNs in brain injury, the role of adhesion molecules in brain injury, and potential TNF-α directed therapeutic strategies for prevention of brain injury. In the brain of HIV-1 infected patients, some microglial cells are infected while many other are activated and express elevated levels of TNF-α. These studies demonstrate a direct involvement of TNF-derived from activated human microglia and TNF-α induced oligodendrocyte damage and death in vitro. Thus TNF-specific inhibitors could slow down viral replication and attenuate cytotoxicity for oligodendrocytes in HIV-1 encephalopathy (S. G. Wilt, et al., *Tech. Adv. AIDS Res. Hum. Nerv. System,* 1995, Pages 151–162.). TNF-α was detected in the spinal fluid (CSF) of patients with bacterial, but not viral, meningitis. In contrast to spinal fluid (CSF), the serum of the patients with bacterial meningitis contained no or only small amounts of TNF-α. In studies of patients with pyogenic meningitis and aseptic meningitis of different etiologies (viral, neoplastic) a positive correlation between the levels of TNF-α and IL-β and a bacterial, but not a viral or neoplastic etiology was observed. Thus these cytokines, especially TNF- , are useful markers for distinguishing between pyrogenic and nonpyrogenic meningitis (sensitivity 94.2%; specificity 100%). Moderately raised CSF TNF-α levels were seen also in patients with Mycobacterium tuberculosis meningitis. TNF-α concentrations in the CSF correlated with CSF protein and endotoxin concentrations, bacterial density and outcome.

Taken collectively, bacterial meningitis is accompanied by intrathecal production of cytokines which may be intimately involved in the development of the meningeal inflammatory response. The prevention of brain edema by anti-TNF-α antibodies in experimental meningitis provides firm evidence for the involvement of TNF-α in the breakdown of the Blood Brain Barrier. TNF-α can also trigger the infiltration of neutrophils into the tissue with consequent induction of secondary mediators in local areas. Endothelial cell damage leading to brain edema is further mediated by production of reactive oxygen intermediates and is prevented by superoxide dismutase ("Cytokines and CNS," Edit: R. M. Ransohoff and E. N. Beneviste, CRC Press, Page 193, 1996).

E. Shohami et al. (*J. Cerebral Blood Flow Metab.,* 16:378–384, 1996) recently demonstrated that closed head injury (CHI) in rats triggers the production of TNF-α in the contused brain hemisphere. The study was designed to determine whether inhibition of TNF-α production or activity affects the development of cerebral edema, as well as neurologic dysfunction and hippocampal cell loss after CHI. Two pharmacologic agents lessened peak edema formation at 24 hours, and facilitated the recovery of motor function for 14 days post-injury. The brain levels of TNF-α were reduced by 80%, an attenuation of the disruption of the Blood Brain Barrier was seen, and the hippocampal cells were protected. Thus, a decrease in TNF-α levels or inhibition of its activity is accompanied by significantly reduced brain damage.

Multiple Sclerosis

Although multiple sclerosis (MS) may be immune mediated, the therapeutic efficacy of immunosuppressive agents has been disappointing thus far (R. Smith, *Lancet,* 347:1251, May 4, 1996). The multiple sclerosis (MS) plaques within the CNS are infiltrated by peripheral blood mononuclear cells. In patients, Glabinski et al. (*Neurol Scand.,* 91:276–279, 1995) found that TNF-α, but not lymphotoxin, is overproduced by peripheral blood mononuclear cells during MS relapse.

TNF-α has a diverse range of functions in the CNS because of its direct effects on oligodendrocytes, astrocytes, and brain endothelial cells. Most relevant to CNS disease is the ability of TNF-α to mediate myelin and oligodendrocyte damage in vitro and its ability to cause cell death of oligodendrocytes in vitro. This aspect of TNF-α activity contributes directly to myelin damage and/or the demyelination process observed in diseases such as multiple sclerosis. Human oligodendrocytes express both types of TNF receptor (TNF-R1 and TNF-R2); thus, the cytotoxicity mediated by TNF-α and TNF-β may occur through activation of TNF-R1.

TNF-α is recognized to be an important mediator of inflammatory responses in a variety of tissues, including the brain, and may play an important role in the initiation of inflammation and the pathologic consequences that result from this process. TNF-α has a diverse range of functions in the central nervous system (CNS) because of its effects on oligodendrocyte microglia and astrocytes. Most relevant to CNS disease is the ability of TNF-α to mediate myelin and oligodendrocyte damage in vitro. TNF-α also has an ability to cause cell death of oligodendrocytes in vitro (Robbins, D. S. et al., *J. Immunol.*, 139:2593, 1987). This aspect of TNF-α activity may contribute directly to myelin damage and/or the demyelination process observed in diseases such as multiple sclerosis (MS). TNF-α also has multiple effects on the astroycte which are noncytotoxic in nature. One of the pathologic features of demyelinated plaques in MS is astrogliosis, in which proliferation of astrocytes and production of glial fibrillary acidic protein occurs, (C. S. Raine, *Lab. Invest.*, 50:608, 1984). Astrocyte proliferation leads to the reactive gliosis associated with MS, and TNF-α enhances this process. Proliferation of astrocytes in vitro in response to TNF-α indicates a primary role for TNF- (K. W. Selmaj et al, *J. Immunol.*, 144:129, 1990).

TNF-α has been shown to play a central role in the demyelination of the CNS in MS. Serum levels of TNF-α are elevated in patients with active MS, and TNF-α producing macrophages, microglia and astrocytes are present at active lesion sites. In vitro experiments, TNF-α directly mediates oligodendrocyte damage and suppresses myelin formation, and it stimulates astrocytes, which are then responsible for the CNS scarring plaques in MS (Owens and Sriram, *Neurological Clinics*, 13:51, 1995).

Key players in the process of demyelination are macrophages and microglia. TNF-α may be a key player in oligodendrite survival or death in autoimmune demyelination, as it has been detected in MS plaques. However, the details of the role of TNF-α in demyelination in vivo remains to be determined ("Cytokines and the CNS," Ed: R. M. Ransohoff and E. N. Beneviste, CRC Press, 1996, p.99).

Serum levels of TNF-α are elevated in patients with active MS (M. Chofflon et al., *Eur. Cytokine Net.*, 3:523, 1991; Sharief, M. K. and Hentgen, *N. E. Jour. Med.*, 325:467, 1991). TNF-α producing macrophages/microglia and astrocytes are present at active lesion sites (K. Selmaj al., *Jour. Clin. Invest.*, 87:949,1991). In in vitro experiments, TNF-α directly mediates oligodendrocyte damage and suppresses myelin formation (K. Selmaj et al., *J. Immunol.*, 147:1522, 1990); T. Tsumamoto et al., *Acta Neurol. Scand.*, 91:71, 1995), and it stimulates astrocytes, which are responsible for the scarring plaques (K. Selmaj et al., *Jour. Immunol.*, 144:129, 1990).

Pathological features of MS include perivascular inflammation and demyelination with oligodendrocyte loss; attempts at remyelination are often unsuccessful and often culminate in astrocytic scarring. In tissue culture, oligodendrocytes are susceptible to injury via cell-mediated and humoral mechanisms. Substances including complement and TNF-α, are capable of killing rat oligodendrocytes in vitro; surface complement activation also initiates intracellular processes within oligodendrocytes as well as providing ligands for phagocytic interactions. (J. Zajicek et al., *Mult. Scler.*, 1:61–72, 1995.)

Astrocytes express only the TNF-R1 (~3,000 receptors/cell); thus, all effects of TNF-α are mediated via this receptor. One of the pathologic features of MS is gliosis, in which proliferation of astrocytes and excessive production of Glial Fibrillary Acidic Protein occur. TNF-α induces astrocyte proliferation, which may lead to the gliosis associated with MS, especially since TNF-α levels in the CNS are elevated during these diseases. TNF-α is a potent inducer of the production of cytokines by astrocytes.

Reickmann and colleagues showed an increase in TNF-expression preceding MS exacerbation attacks (using circulating mononuclear cells). ("Cytokines and the CNS," Edit: R. M. Ransohoff and E. N. Beneviste, CRC Press, 1996, p.232).

The role of TNF-α in regulating astrocyte proliferation has been examined using various types of astrocyte cultures from human and rat brains. In human astrocyte cell lines, TNF-α increases proliferation, and this effect is inhibited by an TNF-α antibody.

In vivo studies of murine, rat and human demyelinating diseases indicate that TNF-α participates in the inflammatory reactions that take place within the CNS. TNF-α positive astrocytes and macrophages have been identified in the brains of MS patients, particularly in the plaque region (F. M. Hofman et al., *J. Exp. Med.*, 170:607, 1991, and Selmaj et al., *J. Clin. Invest.*, 87:949, 1991) have determined that both TNF-α and TNF-β are present in MS plaque regions, and that TNF-α is localized within astroyctes, whereas TNF-α is associated with microglia and T-cells. Increased serum and cerebrospinal fluid levels of TNF-α have been documented in patients with MS (Sharief, M. K., M. Phil, and R. Hentges, *N. Engl. J. Med.*, 325:467, 1991), and a strong correlation exists between cerebrospinal fluid levels of TNF-α, disruption of the blood brain barrier, and high levels of circulating ICAM-1 in patients with active MS.

Alzheimer Disease

Alzheimer's disease (AD), the most common dementing disorder of late life, is a major cause of disability, and death in the elderly. The disease is manifested by the appearance of abnormalities in the brain, particularly involving the hippocampus, amygdala, thalamus and neocortex. Lesions in these regions are associated with dysfunction/death of neurons and deafferentation of targets. The principal pathological hallmarks of AD are deposits of the amyloid-β protein (Aβ) in extracellular parenchyma and cerebral vessels, and neurofibrillary tangles (S. S. Sisodia et al., "Pathobiology of Alzheimer's Disease," Academic Press, Ltd., p.183, 1995).

TNF-α has been generally elevated in the serum of AD patients based upon both antibody assays and bioassays. In one study almost half of the AD cases had elevated TNFα, but none of the controls had a similar elevation. The patients with increased serum TNF-α were free of inflammatory diseases, and it was speculated that increase in serum TNF-α was a reflection of CNS disease. The blood-brain barrier does not normally permit passage of cytokines. However, there is evidence to suggest that the blood-brain barrier may not be intact in AD. The primary mediators of immunological processes within the CNS are the glial cells and in particular, astrocytes and microglia. ("Cytokines and the CNS," Ed. by R. M. Ransohoff and E. T. Beneveniste, CRC Press, Pg. 246, 1996.).

There is a diffuse increase in the number of astrocytes in the cortex of AD, and astrocytes are also frequently associated with senile plaques. Immunocytochemical studies have shown that apo-E is associated with senile plaques and neurofibrillary tangles. ("Cytokines and the CNS," Ed. by R. M. Ransohoff and E. N. Beneviste, CRC Press, Pg. 254, 1996.)

β-protein (Aβ) which is deposited in the amyloid plaques and vasculature in brains of Alzheimer's Disease (AD) patients is a 39 to 43 amino acid peptide proteolytically derived from the amyloid precursor protein (A Greek beta PP). (J. Conn, Amyloid, 1:232–239, 1994.).

Extracellular deposition of amyloid fibrils is associated with the pathological events in the systemic amyloidoses and probably also in Alzheimer's disease (Haas, C & Selkoe, D. J. (1993) Cell 75, 1039–1042) and type II diabetes mellitus (Lorenzo, A., et al., 1994) Nature (London), 368, 756–760).

Deposition of amyloid fibrils in the brain is a histopathological hallmark of Alzheimer's disease (AD), and β-amyloid is implicated in the neuropathogenesis of AD. Ab-induced neurodegeneration was accompanied by microglial cell proliferation and enhanced release of TNFα (C. Chun, Mol. Chem. Neuropathol., 23:159–178, 1994).

The progression of Alzheimer's disease and related disorders involves amyloid β-protein (Aβ) deposition and pathological changed in the parenchyma as well as cerebral blood vessels. The cerebrovascular Aβ deposits in these disorders are associated with degenerating smooth muscle cells in the vessel wall, which have been shown to express the Aβ precursor (AβPP) and Aβ. The authors show that Aβ1-42, an abundant cerebrovascular form of Aβ, causes cellular degeneration in cultured human cerebrovascular smooth muscle cells. This stress response is accompanied by a striking increases in the levels of cellular AβPP and soluble. Aβ peptide produced in these degenerating cells. These data provide the first experimental evidence that Aβ can potentially contribute to the onset and progression of the cerebrovascular pathology (S. Saporito-Irwin, et al., J. Neurochem., 65:931–934, 1995).

Disruption of vascular function may underlie neurodegenerative diseases such as Alzheimer's. T. Thomas et al. (Nature, 380:168–171, 1996), have shown that β-amyloid may alter the structure and function of endothelium in blood vessels by stimulating the production of superoxide radicals. Their observations provide a link between the free-radical theory of aging and Alzheimer-type neurodegeneration.

β-amyloid deposits are seen in the brain and cerebral blood vessels of aging individuals and Alzheimer patients. As abnormalities in the microvasculature of the brain are an early indicator of Alzheimer's disease, Thomas'et al., supra, investigated the effect of β-amyloid on blood vessels. They found that micromolar concentrations of β-amyloid caused rapid vasoconstriction of rat aorta. To test whether superoxide radicals were involved in this effect, blood vessels were preincubated with superoxide dismutase, a free-radical scavenger. β-amyloid-induced vasoconstriction was blocked. Electron microscopy revealed a clear damage to the endothelium in β-amyloid-treated blood vessels. (J. Bradbury, Lancet, 347:750, 1996.)

Disorders of the Respiratory System (Pulmonary Function and Perfusion (DLCO))

Villani et al, (Jour. Chemotherapy, 7:452–454, 1995, studied pulmonary function in 22 patients affected by in-transit metastes from cutaneous melanoma and metastases from soft tissue sarcoma of the limbs who were treated with isolation perfusion in extracorporeal circulation with TNF-α at doses ranging from 0.5 to 4.0 mg/square meter in mild hyperthermia. Seventeen patients suffered respiratory insufficiency which required assisted ventilation (7 mechanical ventilation for 1 day, 8 for 2 days and 2 patients on synchronized intermittent mandatory ventilation). Seriometric parameters recorded 7 to 125 days after treatment did not change from baseline values; in contrast, lung transfer factor (DLCO) for carbon monoxide significantly declined in a dose-dependent fashion. These data confirm that TNF-α administered by isolation perfusion technique induces pulmonary side effects (previously described by R. C. Morice, et al., Proc. Soc. Clin. Oncol., 6:29, 1987; Kuei et al., Chest 96:334–338, 1989; Lienard et al., World Jour. Surg., 16:234–240, 1992).

One potential therapeutic strategy is to selectively inhibit the actions of macrophage-derived cytokines. The importance of the pathophysiologic concentrations of TNF- has been demonstrated (Vilcek J. et al., Jour. Exp. Med., 163:632–643, 1986). Piguet et al., (Jour. Exp. Med., 170:655–665, 1989; Nature, 344:245–247, 1990) utilized in vivo administration of TNF-α antibodies to abolish lung fibrosis in a murine model of hypersensitivity pneumonitis. Diffusion capacity is more accurately described by the appellation "transfer factor", since it may be affected by factors other than impairment of gas diffusion. The diffusing capacity of the lung for carbon monoxide (DLCO), usually measured by the single-breath method, is commonly utilized because it is more easily measured. DLCO is usually reduced at the time of diagnosis of pulmonary dysfunction and is reduced to a greater extent than lung volume. DLCO has a been a remarkable clinical tool in the follow-up of the pathological severity in bleomycin-induced human pneumonitis (Van Barneveld et al, Am. Rev. Respir. Dis., 135:48–51, 1987).

Impairment of gas diffusion (carbon monoxide, carbon dioxide or oxygen) is caused by abnormalities of the alveolar-capillary membrane, reduction in the pulmonary capillary blood volume, erratic distribution of diffusing capacity relative to lung volume, or perfusion.

The membrane component of diffusing capacity may be reduced either by increased thickness of the alveolar-capillary membrane or by a reduction in the total surface area available for gas exchange. Cassan et al., Chest, 65:275–278, 1974) in a morphometric study of lung biopsy specimens from nine patients with moderately severe dysfunction of pulmonary diffusion, found the harmonic mean thickness of the alveolar-capillary membrane increased by 70% over that of normal controls.

The DLCO values correlate strongly with the severity of exercise-induced deterioration of gas exchange. This is measured as the change in PaO2, arterial oxygen saturation between rest and exercise, and is directly correlated to the oxygen demand, and the efficiency of oxygen diffusion.

For monitoring the course of pulmonary function patients, measurements should consistently include determination of DLCO values. Such measurements are widely available, easy to perform and inexpensive (Gottlieb, D., et al, Pulmonary Fibrosis, 80:85–87, 1995). The response to therapy over 6–12 months usually is predictive of the course over the subsequently 24 months (Rudd et al., Am. Rev. Resp. Dis., 124:4–8, 1981); Watter et al., Am. Rev. Resp. Dis., 135:696–4704, 1987). Deterioration over the first year of therapy is predictive of reduced long-term survival.

TNF-α has been shown to play a role in pulmonary fibrosis induced by bleomycin and silica (Piguet et al., *Jour. Exper. Med.*, 170:655–663, 1989, and *Nature*, 344:245–247, 1990; Everson and Chandler, *Amer. Jour. Path.*, 140:503–512, 1992; Phan and Kunkel, *Exp. Lung Res.* 18:29–43, 1992; also, Warren et al., *Jour. Clin. Invest.*, 84:1873–1882, 1989; Denis et al., *Amer. Jour. Cell Mol. Biol.*, 5:477–483, 1991).

TNF-α has been reported to orchestrate its proinflammatory effects by regulating the compartmentalized release of secondary messenger cytokines. Investigations have shown that nude mice exposed to chronic in vivo TNF- develop pulmonary inflammation and fibrosis (ARRD 145:A307, 1992).

Asthma

Cirelli et al. undertook to characterize more fully the patterns of monokine production in the allergic asthmatic airway, and hypothesized that the relative levels of these substances may be related to disease classification and cellular recruitment. Cytokine measurements were made by ELISA of 10× concentrated BAL fluid obtained before (day 1) and 24 hours after segment antigen challenge (day 2) with ragweed in 25 allergic asthmatics, 19 with a dual response to whole lung challenge, 6 with single early response. Results: the levels of TNF-α, IL-1b and IL-1ra were increased on day 2 for all asthmatics (TNF-α: 2.49±0.75 to 12.43±4.78 pg/ml, p=0.03; IL-1b: 3.70±0.62 to 7.25±0.91 pg/ml, p=0.02; IL-1ra: 1531.83±270.34 to 3799.96±440.49 pg/ml, p=0.0001). While there was a trend towards increasing cytokine levels among AA-S, day 2 levels of TNF-α, IL1 and IL-1ra were higher in the AA-D group (p<0.05 for all three) and accounted for the majority of the day 2 increases. Cellular influx was also greatest among the AA-D (p<0.05 for macrophage, eosiniphil, and neutrophil). Investigators concluded that the production of TNF-α, IL1 and IL-1ra is significantly increased 24 hours after segmented antigen challenge in all allergic asthmatics. (R. A. Cirelli, et al., *Amer. Jour. Resp. Critical Care Med.*, 151:345A, 1995).

TNF-α is a pro-inflammatory cytokine which is believed to play an important role in asthma. Concentrations of TNFα were measured in bronchoalveolar lavage (BAL) fluid in 13 healthy control subjects (4M/9F, mean age 22.5±SD 4.0; 8 atopic and 7 mildly symptomatic atopic asthmatics age 30.7±13.2). Fiberoptic bronchoscopy was carried out under local anesthesia and BAL was performed in a segmental bronchus of the right upper lobe. BAL fluid was concentrated 10–30 times and concentrations of TNF-a were measured by an ELISA technique. TNF-α levels (expressed per ml unconcentrated BAL fluid) were significantly greater in the asthmatics compared to the control subjects (median 97.5 vs. 54.1 fg/ml, p<0.05). However, there was no significant difference between TNF-α levels in the non-atopic and the atopic control subjects (54.1 vs. 57.4 fg/ml, p>0.05). These findings indicate an increased tissue level of TNF-α in asthma and that this may contribute to the pathophysiology of the condition. (A. E. Redington et al., *Amer. Jour. Respir. Crit. Care Med.*, 151: 702A, 1995).

Chronic Obstructive Pulmonary Disease (COPD)

Another disease state in which TNF-α plays a role in the pathophysiology is chronic obstructive pulmonary disease. In silicosis, a disease of progressive respiratory failure caused by a fibrotic reaction, antibody to TNF-α completely blocked the silica-induced lung fibrosis in mice (Piguet et al., *Nature*, 344:245–247, 1990). High levels of TNF- production (in the serum and in isolated macrophages) have been demonstrated in animal models of silica and asbestos induced fibrosis (Bissonnette et al., *Inflammation*, 13:329–339, 1989).

Inflammation in COPD patients is currently assessed by endoscopic bronchial biopsies. An increase of inflammatory cells and an upregulation of adhesion-molecules both on endothelial and epithelial cells are found. In this study, authors evaluated the levels of systemic inflammation by measurement of inflammatory mediators in plasma of patients with stable COPD (*Amer. Jour. Respir. Crit. Care Med.*, 151: 841A, 1995).

Adult Respiratory Distress Syndrome (ARDS)

Adult respiratory distress syndrome where excessive TNF-α concentrations in excess of 12,000 pg/ml have been detected in pulmonary aspirates from ARDS patients (Millar et al., *Lancet*, 2(8665):712–714, 1989). Systemic infusion of recombinant TNF-α resulted in changes typically seen in ARDS (Ferrai-Baliviera et al., *Arch. Surg.*, 124:1400–1405, 1989).

Lung Sarcoidosis

Alveolar macrophages from pulmonary sarcoidosis patients have been found to spontaneously release massive quantities of TNF-α as compared with macrophages from normal donors (Baughman et al., *Jour. Lab. Clin. Med.*, 115:36–42, 1990); TNF-α also implicated in other acute disease states such as the pathophysiologic responses which follows subsequent reperfusion. It is involved in reperfusion injury, and is a major cause of tissue damage after loss of blood flow. (Vedder et al., *Proc. Nat. Acad. Sci.*, 87:2643–2646, 1990).

Sepsis

Overproduction of TNF-α has been implicated in the pathogenesis of endotoxin induced septic shock, (see Carswell et al., *Proc. Nat. Acad. Sci.*, 2:3666–3670, 1975). Endotoxin is the lipopolysaccharide component of the cell wall of gram-negative bacteria, and is a macrophage activator which induces the synthesis and enhanced secretion of TNF-α and other biologically active cytokine molecules. TNF-α is recognized as a central mediator of sepsis, septic shock and multiple organ failure. These host reactions are associated with increased blood levels of TNF-α, due to increased TNF-α production. (F. Stuber et al., *Jour. Inflam.*, 46:42–50, 1996).

In sepsis, TNF-α overproduction leads to hypotension, vascular endothelial permeability, and organ damage, i.e., some of the results of endotoxic shock. Adult Respiratory Distress Syndrome (ARDS) is frequently associated with sepsis and multiple organ failure which has led to recognition of a role for TNF-α in the pathogenesis of ARDS. TNF-α is also the agent responsible for the weight loss (cachexia) found in chronic catabolic disease states, such as long term parasitic and viral infections and malignancies. This weight loss is a handicap to recovery and may even be fatal.

The liver contains the largest pool of cytokine-producing macrophages in the body, and may therefore play an important role in the development and outcome of sepsis syndromes. S. Auer-Bath et al. investigated the TNF- releasing capacity of the in situ perfused mouse liver. Pre-treatment of mice with either LPS or TNF-α elicited a dose-dependent TNF-α release into the perfusate (*Jour. Pharm. Exper. Therap.*, 276:968–976, 1996).

A. M. Badger et al. studied the effect of on specific agents for their effects on LPS-induced TNF-α production in vitro and in vivo, and for their ability to protect mice from LPS-induced lethality in D-galactosamine sensitized mice. In vivo, effective agents greatly reduced TNF-α serum levels. TNF-α is implicated as having a central pathogenic role in the LPS plus D-galactosamine model, since survival of the animals correlated directly with the reduction of serum TNFα levels (*Cir. Shock*, 44:188–195, 1994).

In Vivo, there was a rank order potency on serum TNF levels in LPS challenged D-galactosamine sensitized mice. Interestingly, TNF is implicated as having a central pathogenic role in the LPS/D-galactosamine model, since survival of animals correlated directly with reduction of serum TNF levels for each compound studied (Badger et al., *Circ. Shock*, 44:188–195, 1994).

A highly specific polyclonal rabbit anti-serum directed against murine TNFα was prepared. When BALB/c mice were passively immunized with antiserum, they were protected against the lethal effect of the LPS derived from *E. coli*. The prophylactic effect was dose-dependent and was most effective when the antiserum was given prior to the injection of the LPS. Anti-serum to TNF-α did not mitigate the febrile response of LPS-treated animals, and very high doses of LPS could overcome the protective effect. The median lethal dose of LPS in mice pre-treated with 50 microliters of specific antiserum was approximately 2.5 times greater than the median lethal dose for controls given nonimmune serum. The data suggest that TNF-α is one of the principal mediators of the lethal effect of LPS (B. Beutler et al., *Science*, 229:869, 1985).

Liver

Because of its central role in metabolism and host defense mechanisms, the liver is thought to be major organ responsible for initiation of the multiple organ failure during sepsis. The depression in hepatocellular function in early, hyperdynamic stages of sepsis does not appear to be due to any reduction in hepatic perfusion, but is associated with elevated levels of circulating cytokines such as TNF-α

Furthermore, administration of recombinant TNFα at doses that do not reduce cardiac output or hepatic perfusion, produces hepatocellular dysfunction. (P. Wang et al., *Amer. Jour. Physiol.*, 270:5, 1996).

The liver contains the largest pool of cytokine-producing macrophages in the body and may therefore play an important role in the development and outcome of systemic inflammatory response syndromes. The TNf-α releasing capacity of the in situ perfused mouse liver and its modulation by methylxanthines was investigated, i.e., by a class of well-established inflammatory cytokine-suppressing drugs. It was shown that pre-treatment of mice with either lipopolysaccharide or TNF elicited a dose-dependent TNF release into the perfusate which was inhibited by in vivo pretreatment of mice with pentoxifyline or A-802715 (i-(5hydroxy-5-methyl)hexyl-3-methyl-7 proplyxanthin). Infusion of these methyl-xanthines into livers from mice pretreated with lipopolysaccharide or TNF also inhibited TNF release in an immediate and reversible way even after TNF production had been initiated. The inhibitory effect of methyl-xanthines was prevented by pretreatment with the adenylate cyclase inhibitor dideoxyadenosine, suggesting upregulation of the cyclic adenosine monophosphate system as a possible mechanism of action of these drugs. It was demonstrated that the liver is a potent cytokine producer and identify it as one of the target organs of methyl-xanthines or other phosphodiesterase inhibitors in murine models of shock and inflammatory liver failure. (M. Leist, *J. Pharmacol. Exp. Ther.*, 276:968–976, 1996.).

The authors discuss TNF-α induction of hepatic apoptosis under transcriptional arrest, activation of the 55 kDa receptor in the induction of hepatic apoptosis, the glycosylation step in TNF-induced hepatic apoptosis, hepatic injury induction by T cell-initiated cytokine release, and Ta cell-dependent TNF-mediated liver injury without transcriptional arrest. (A. Wendel et al., *Cell. Biol. Mol. Basis Liver Transp.*, Int., Ringberg Conf. Hepatic Transp., 2nd, 1995, Pages 105–111.).

Pancreas

The mechanism of obesity-induced resistance to insulin which puts obese individuals at risk for developing heart disease and type II diabetes has been identified recently (*Science* 271:665, 1996). Knowing that the fat cells of obese individuals contain TNF-α at levels that correlate with the degree of both obesity and insulin resistance, the researchers tackled the role of TNF-α in promoting insulin resistance. They found that TNF-α induces resistance by phosphorylating a key substrate, at serine residues. This altered form of IRS inhibits the first step in the insulin pathway autophosphorylation of the insulin receptor after insulin binds to it.

TNF-α plays a central role in the state of insulin resistance associated with obesity. It has been previously shown that one important mechanism by which TNF-α interferes with insulin signaling is through they serine phosphorylation of insulin receptor substrate-1 (IRS-1), which can function as an inhibitor of the tyrosine kinase activity of the insulin receptor (IR). The data strongly suggest that TNF-α inhibits signaling via a stimulation of p55 TNFR, and sphingomyelinase activity, which results in the production of an inhibitory form of IRS-1 (P. Peraldi et al., *Jour. Biol. Chem.* 271:13018–13022, 1996).

Crohn's Disease

Investigators measured TNF-α concentrations in stool samples from normal children, infants with diarrhea, and children with inflammatory bowel disease in active and inactive phases. In 10 normal children and 14 children with diarrhea, median stool TNF-α concentrations were 58 and 45 pg/gram stool, respectively. Compared with diarrhea controls, stool TNF-α concentrations were significantly increased in children with active Crohn's disease (n=13, median 994 pg/gram, P<0.0002). In patients with inactive Crohn's disease, either as a result of surgery, or treatment with steroids, the concentration of stool TNF-α fell to the level of the controls (approximately 50 pg/gram; C. P. Braegger et al., *Lancet*, 339:89–91, 1992).

Pre-Eclampsia

Pre-eclampsia is an endothelial disorder, and TNF-α has fundamental effects on endothelial cells by several means, including alteration of the balance between oxidant and anti-oxidant, changing the pattern of prostaglandin production, and affecting the expression of several cell surface components. In patients, results show that TNF-α mRNA expression is significantly elevated in preeclamptic patients compared to the control groups. These observations are consistent with a major role for TNF-α in the development of eclampsia (G. Chen et al., *Clin. Exp. Immunol.* 104:154–159, 1996).

Dermal Burns

The protein catabolic rate and TNF-α content of the soleus muscle of the scalded region and remote region were dynamically determined in the first week after the rats were inflicted with 37% TBSA full thickness scalding. The TNF-α content of skeletal muscles was far greater in the scalded region than in the remote region. TNF-α increase was also significantly correlated to the protein catabolic rate of the skeletal muscles (L. LI et al., *Jour. Med. Coll.*, PLA 10:262–267, 1995; C.A. 125:938, 1245:8156a, 1996).

Bone Resorption

TNF-α is increased in bone resorption diseases, including arthritis, wherein it has been determined that when activated, leukocytes will produce a bone reabsorbing activity. Data indicates that TNF-α enhances this activity (Bertolini et al., *Nature*, 319:516–518, 1986, and Johnson et al., *Endocrinology*, 124:1424–1427, 1989). TNF-α stimulates bone resorption and inhibits bone formation in vitro and in vivo through stimulation of osteoclast formation and activation combined with inhibition of osteoblast function. TNF-α may be involved in many bone resorption diseases, including arthritis.

Rheumatoid Arthritis

Analysis of cytokine mRNA and protein in human rheumatoid arthritis tissue revealed that many proinflammatory cytokines such as TNF-α care abundant in all patients regardless of therapy. In rheumatoid joint cell cultures that spontaneously produce IL1, TNF-α as the major dominant regulator of IL1. Subsequently, other proinflammatory cytokines were also inhibited if TNF-α was neutralized, leading to the concept that the proinflammatory cytokines were linked in a network with-TNF-α at its apex. This led to the concept that TNF-α was of major importance in rheumatoid arthritis and was a therapeutic target. This has been successfully tested in animal models of collagen-induced arthritis, and these studies have provided the rationale for clinical trials of anti-TNF-α therapy in patients with long-standing rheumatoid arthritis.

Several clinical trials using a chimeric anti-TNF-α antibody have shown marked clinical benefit, verifying the concept that TNF-α is of major importance in rheumatoid arthritis. Re-treatment clinical studies have also shown benefit in repeated relapses, indicating that the disease remains TNF-α dependent (M. Feldmann, *Annual Rev. Immunol.*, 14:397–440, 1996.).

Vascular

TNF-α alters the properties of endothelial cells and has various pro-coagulant activities, such as production an increase in tissue factor procoagulant activity and suppression of the anticoagulant protein C pathway as well as down-regulating the expression of thrombomodulin (Sherry et al., *Jour. Cell. Biol.*, 107:1269–1277, 1988). TNF-α has activities which, together with its early production (during the initial stages of a trauma or injury event), make it a mediator of response to tissue injury in several important disorders including, but not limited to myocardial infarction, stroke and circulatory shock. Of specific importance may be TNFα induced expression of adhesion molecules, such as intercellular adhesion molecule (ICAM) or endothelial leukocyte adhesion molecule (ELAM) on endothelial cells (Munro et al., *Am. Jour. Path.*, 135:121–132, 1989).

Cardiac

Packer et al. indicate the current top suspects in heart failure are noradrenaline, angiotensin, vasopressin, endothelin, and tumor-necrosis factor (TNF-α), (*N.E. J. Med.*, 323:236–241, 1990). They reported that concentrations of TNF-α, which cause cachexia in chronic inflammatory disorders, infections, cancer and other diseases, were elevated in patients with severe heart failure, especially those with the more severe manifestations of the disease, such as cardiac cachexia.

The main purpose of this study was to determine the subchronic effects of low concentrations of TNF-α on the inotropic response and on the cellular level of high energy phosphates of cardiomyocytes. Therefore, the inotropic response of cultured neonatal rat heart cells to 10–5M isoproterenol-, 10–1M ouabain-, 10–5M forskolin- and 2,4 mM calcium-perfusion was studied 24 hours after exposure to TNF-α. From results with animals and humans, it is concluded that subchronic exposure to low concentrations of TNF-α results in an almost complete but reversible inhibition of the response of cardiomyocytes to difference inotropic agents suggesting that a common final step of the inotropic cascade might be altered by TNF-α. Although energy metabolism of TNF-α exposed cells was affected also, reduction of high energy phosphate levels alone it not explain the observed inhibition of the inotropic response of the cardiomyocytes. The investigators conclude from studies in vitro with cultured rat cardiomyocytes that subchronic exposure to low concentrations of TNF-α resulted in almost complete, but reversible, inhibition of the response of the cardiomyocytes to different inotropic agents (isoproterenol, ouabain, forskolin), suggesting that a common final step of the inotropic cascade might be altered by TNF-α, (P. Boekstegers, *Mol. Cell. Biochem.*, 156:135–143, 1996.).

Inflammatory disease states predispose to myocardial infarction. The authors investigated the effects of a systemic inflammatory response syndrome, (LPS)-induced circulatory shock in rats, on coronary vascular tone. Pre-treatment with cycloheximide or a TNF-α antibody or continuous infusion in vivo and in vitro of the endothelin ETA receptor selective antagonist FR 139317, greatly decreased the increase in coronary vascular resistance induced by LPS. Thus TNF-α may induce the release of endothelin-1-(ET-1) and this mediates at least part of the coronary vasoconstriction. Therefore, in inflammatory disease states, such as LPS-induced septic shock, there is the sequential release of TNF-α and endothelin-1 which leads to an increase in coronary vascular tone and so a predisposition to myocardial ischemia. Inactivation of TNF-α by an antibody as well as ET, receptor blockage by a selective antagonist may effectively interfere with this pathway. (T. Hohlfeld, et al., *Br. J. Pharmacol.*, 116:3309–3315, 1995.).

Immunology

In graft versus host reactions, increased serum TNF-α levels have been associated with major complications following acute allogenic bone marrow transplants (Holler et al., *Blood,* 75:1011–1016, 1990).

Although salmeterol, and the related agents did inhibit TNF-α secretion by lipopolysaccharide (LPS)-activated THP-1 cells with similar 1C50S of approx. 0.1 uM. This inhibition was effectively reversed by the B2-antagonist B2-adrenergic receptor. A strikingly different reactivity profile was seen with T cells. Salmeterol was able to inhibit the activation of both mouse and human T cells, as measured by proliferation and IL-2 secretion in response to anti-CD3 antibody, where as albuterol was completely inactive in these assays. This T cell inhibition by salmeterol was about 10-fold less potent than that from TNF-α production, and was not reversed by a B2-antagonist, indicating that a different mechanism was involved in the effect of salmeterol on T cells. Paralleling the TNF-α inhibitory activity in vitro, oral dosing of salmetrerol and albuterol inhibited LPS-induced increase in murine serum TNF-α level in vivo, with ED50s of approximately OS1 mg/kg. This inhibition could be abrogated by dosing orally with the b blocker propranolol. The long-acting pharmacology profile of salmeterol was apparent in that it maintained its efficacy for 3 h, while albuterol had a much shorter duration of action. Salmeterol also had some protective effects in the galactosamine/LPS model of endotoxic shock, which is dependent upon TNF-α production. Though salmeterol inhibited serum TNF-α levels by up to 94% in this assay, it protected less than 50% of the animals from the lethal effects of the LPS/galactosamine mixture. This observation suggests that functional levels of TNF-α localized in tissues may not be accurately reflected by serum levels. (L. Sekut, *Clin. Exp. Immunol.*, 99:461–466, 1995.).

Infections

Some viruses are sensitive to upregulation by TNF-α or will elicit TNF-α overproduction and secretion in vivo. Such viruses include, but are not limited to, HIV viruses, cytomegalovirus (CMV), influenza, adenovirus and the Herpes group of viruses, such as, but not limited to, Herpes zoster and Herpes simplex.

Monocytes, macrophages, and related cells, such as Kupffer and glial cells, have been implicated in maintenance of HIV infections, and are targets for HIV viral replication. TNF-α also has been shown to activate HIV replication in monocytes and/or macrophages (Poli et al., *Proc. Nat. Acad. Sci.*, 87:782–784, 1990). Therefore, inhibition of TNF-α overproduction or activity enhances the suppression of the HIV progression.

AIDS viral replication of latent HIV in T-cell and macrophage lines can be induced by TNF-α (Folk et al., *Proc. Nat. Acad. Sci.*, 86:2365–2368, 1989). A molecular mechanism for the virus inducing activity is indicated by TNF-α's ability to activate a gene regulatory protein found in the cytoplasm of cells, which promotes HIV replication through binding to a viral regulatory gene sequence. (Osborn et al., *Proc. Nat. Acad. Sci.*, 86:2336–2340, 1989). Elevated TNF-α levels in AIDS associated cachexia is suggested by elevated serum TNFα, and high levels of spontaneous TNF-α production in peripheral blood monocytes from patients (Wright et al., *J. Immunol.*, 141:99–104, 1988).

Lahdevirta et al., in the *Amer. Jour. Med.*, 1988, discuss that TNF-α is involved in the HIV-associated states of cachexia and muscle degradation. Wright et al., in the *J. Immunol.*, 141:99–104, 1988, suggest a possible role for TNF-α in AIDS cachexia by elevated serum TNF- and high levels of TNF-α production in peripheral blood monocytes from such patients. Folks et al., (*Proc. Nat. Acad. Sci.*, 86:2365–2368, 1989) indicate that TNF-α induces stimulation of viral replication of latent HIV in T-cell and macrophage lines.

Bacterial meningitis is accompanied by intrathecal production of cytokines which may be intimately involved in the development of the meningeal inflammatory response. The prevention of brain edema by anti-TNF-α antibodies in experimental meningitis provides firm evidence for the involvement of TNF-α in the breakdown of the Blood Brain Barrier. TNF-α also can trigger the infiltration of neutrophils into the tissue with consequent induction of secondary mediators in local areas. TNF-α may also activate formation of platelet activating factor (PAF) and prostaglandins by endothelial cells and leukocytes. Endothelial cell damage leading to brain edema is further mediated by production of reactive oxygen intermediates, which can be prevented by superoxide dismutase (A. Fontana et al.,. "Cytokines and the CNS," Ed., R. M. Ransohoff and E. N. Benveniste CRC Press, 1996, p.193).

TNF-α is also associated with yeast and fungal infections. Specifically, *Candida albicans* has been shown to induce TNF-α overproduction in vitro in human monocytes and natural killer cells (Riipi et al., *Infection and Immunity*, 58:2750–54, 1990; Jafari et al., *Jour. Infect. Dis.*, 164:389–95, 1991; Wasan et al., *Antimicrob. Agents and Chemo.*, 35:2046–48, 1991; and Luke et al., *Jour. Inf. Dis.*, 162:211–214, 1990).

Cerebral malaria is a lethal hyperacute neurological syndrome associated with high blood levels of TNF-α. This is the most severe complication occurring in malaria patients. A form of experimental cerebral malaria that reproduces some features of the human disease was prevented in mice by administration of an anti-TNFα antibody (Grau et al., *Immunol. Rev.*, 112:49–70, 1989). Levels of serum TNF-α correlated directly with the severity of disease and prognosis in patients with acute malaria attacks (Grau et al., *New Eng. Jour. Med.*, 320:1586–1591, 1989).

At conventional doses, the TNF-α suppressant activity of chloroquine in human peripheral blood monocytes stimulated by lysed erythrocytic forms of Plasmodium falciparum were greater than those of quinine. The optimal treatment for cerebral malaria may be a combination with a rapid acting anti-TNF- antibody with chloroquine (D. Kwaitkowski and C. Bate, *Trans. R. Soc. Trop. Med. Hyg.*, 89:215–216, 1995).

One of the hallmarks of Chagas disease (caused by *T. cruzi*) is progressive cardiomyopathy. The disease is associated with elevated serum levels of TNFα, which is known to depress cardiac function. In one month old male, Lewis rats infected with *T. cruzi* trypomastigotes, and killed 15 days later, histological examination of infected animals revealed dense infection with amastigotes within myocytes, and minimal inflammatory infiltrate in the myocardium. In addition to mechanical damage, infection by *T. cruzi* induces pro-inflammatory cytokine production in the myocardium itself, which may further exacerbate the pathology, and adversely affect myocardial function (B. Chandrasekar et al., *Biochem. Biophys. Res. Commun.*, 223:365–3671, 1996).

Accordingly, it is a principal object of the present invention to provide compositions and methods for the (1) inhibition of the synthesis, storage and release of TNF-α from the various appropriate cells (mesenchymal, mesodermal or epithelial in origin), and (2) to prevent the pathophysiologic effects of excessively high concentrations of TNF-α on cells, tissues and organs.

It is an additional object of the invention to provide such compositions and methods that do not inhibit any beneficial effects of TNFα.

Other objects of the present invention, as well as particular features, elements, and advantages thereof, will be elucidated in, or be apparent from, the following description.

SUMMARY OF THE INVENTION

The present invention achieves the above objects, among others, by providing, in a preferred embodiment, a method for the inhibition of the synthesis and release of tumor necrosis factor from various cells, comprising: administering to a human or other mammal an effective dose of one or more pharmaceutical substances selected from the group consisting of N-substituted 2(1H)pyridones, N-substituted 3(1H)pyridones, and pharmaceutically acceptable salts thereof.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which:

FIG. 2A is a chart showing the effect of pirfenidone on TNF-α.

FIG. 3 is a chart showing the inhibition of LPS-induced serum TNFα by pirfenidone.

FIG. 5 presents charts showing the effect of pirfenidone on intracellar TNF-α without administration of LPS and after administration of TNF-α.

DETAILED DESCRIPTION OF THE PREFERRED EMBODIMENTS

Figure 1:
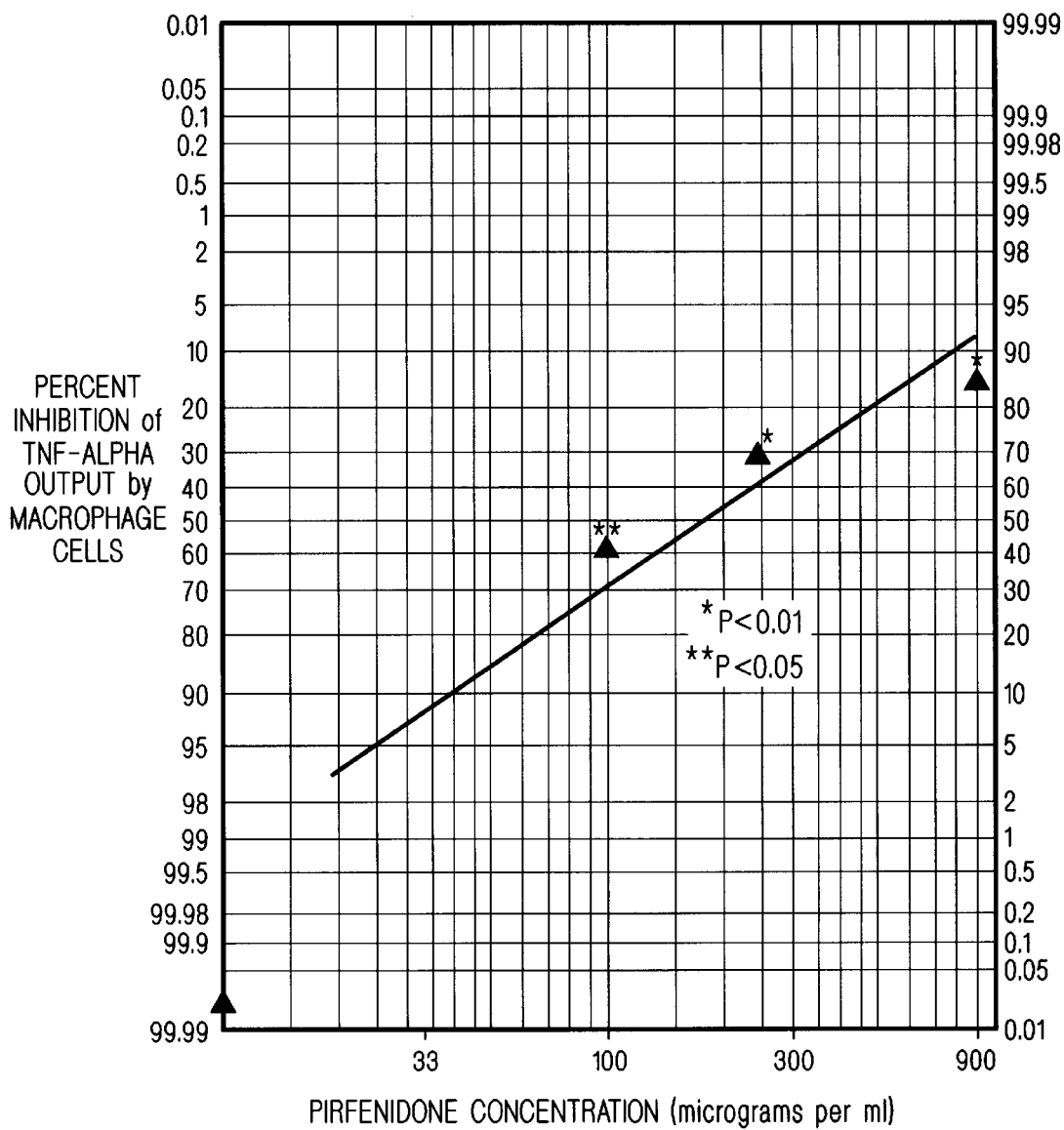
FIG. 1 is a graph of pirfenidone concentration versus percent inhibition of TNF-α output by macrophage cells.

5-Methyl-1-phenyl-2-(1H)-pyridone, "pirfenidone", and related compounds have been found to inhibit the synthesis and release of TNF-α and inhibit or block the several pathophysiological effects of TNF-α at injury sites and thus also inhibit the release of other pathophysiological biochemical products from cells such as histamines, prostaglandins, bradykinins, and peroxidases. The invention also relates to pharmaceutical compositions comprising such compounds and a pharmaceutically acceptable diluent.

The discovery of such compounds which specifically inhibit TNF-α overproduction and/or release not only provides a therapeutic approach for diseases in which excessive TNF-α production is implicated, but also prevents the pathophysiologic effects of exposure to excessive concentrations of TNF-α by cells, tissues or organs. The compounds are useful in inhibiting the overproduction and release of TNF-α by monocytes, macrophages, neuronal cells, endothelial cells, epidermal cells, mesenchymal cells (for example: fibroblasts, skeletal myocytes, smooth muscle myocytes, cardiac myocytes) and many other types of cells.

This invention also relates to a therapeutic method of (1) inhibiting TNF-α and/or TNF-α overproduction and/or its release from cells and (2) preventing the untoward, toxic or lethal effects of excessively high tissue levels of TNF-α in a mammal, including a human. This method comprises administering to a mammal an effective TNF-α inhibiting quantity of one or more of the above compounds. This method also may be used for the prophylactic treatment or prevention of certain TNF-α mediated or exacerbated diseases amenable thereto. The invention provides a method for the treatment of allergic, traumatic, radiation, chemical, microbial and other injurious disorders by safely administering to a mammal, including a human, in need thereof an effective amount of such compounds.

The compounds, by inhibiting or blocking the release, synthesis, as well as the pathophysiologic actions of excessive levels of TNF-α in each of these circumstances, directly facilitate the arrest or resolution of the tissue or organ damage, and facilitates the restoration of normal function. Together, these actions relate their novel use in treating tissue trauma, or other injury disorders caused by infection, allergy, immunologic phenomena, burns, radiation exposure,neoplastic disease, toxic chemicals and expressed as cardiovascular damage, neurologic injury, renal damage, liver damage, pancreatic damage; as well as ascites, localized edema, dermal damage and dermal blisters.

In contrast to cyclophosphamide (Cytoxan), azathioprine, cyclosporine or prednisone which are powerful immunosuppressants, these compounds afford a medicinal remedy for clinical disorders classified as "auto-immune diseases" without suppression of the immune response.

The markedly reduced local edema after systemic or topical use of these novel compounds is evident whether the edema is induced experimentally by a specific chemical agent, an allergic reaction, an endotoxin, radiation, a microbial infection, a thermal burn or by trauma. The edema readily dissipates after (1) local topical application of such a compound or (2) adequate systemic (oral or parenteral) dosage.

For example, such a compound, a TNF-α antagonist, applied locally or given systemically, dramatically eliminates local edema, or vesicant responses (blisters) caused by repeated pressure trauma injury (for example, pressure bruises, or blisters on hands caused by handling of tools), injury caused by scalding or burns, as well as (1) injury caused by chemicals, (2) products released by microbial infection (for example, LPS), (3) immunologic response to contact with a foreign biological product (contact dermatitis, insect bite), (4) classical allergic response (ragweed hay fever resulting in chronic rhinitis), (5) radiation exposure (sunburn).

In patients with pulmonary dysfunction, preliminary tests with oral pirfenidone demonstrated marked, rapid and consistent improvement in the diffusion capacity of the lungs as measured by serial DLCO determinations.

The compounds also are useful in the treatment of viral infections, where such viruses are sensitive to upregulation by TNF-α or will elicit TNF-α overproduction and secretion in vivo. The viruses for treatment with the cited compounds are those that produce TNF-α as a result of infection, or those which are sensitive to inhibition, such as by decreased replication, directly or indirectly, to the TNF-α inhibitors of Formula (I). Such viruses include, but are not limited to HIV viruses, cytomegalovirus (CMV), influenza, adenovirus and the Herpes group of viruses, such as, but not limited to, Herpes zoster and Herpes simplex.

The active compounds described herein inhibit production of TNF-α and are therefore of use in the treatment of very many diseases associated with excessive TNF-α tissue or blood levels, described above, and which include septic shock, hemorrhagic shock, rheumatoid arthritis, insulin resistance in type 2 diabetes, inflammatory diseases, adult respiratory distress syndrome, asthma, post-renal dialysis syndrome, and graft versus host disease after bone marrow transplantation.

In order to use such a compound or a pharmaceutically acceptable salt thereof for the treatment of humans and other mammals, it is normally formulated in accordance with standard pharmaceutical practice as a pharmaceutical composition. The compounds or a pharmaceutically acceptable formulations thereof can be used in the manufacture of medications for the prophylactic or therapeutic treatment of any disease state in a human or other mammal, which is mediated by inhibition of TNF-α, such as but not limited to asthma, allergic, or inflammatory diseases. The compounds are administered in an amount sufficient to treat such a disease in a human or other mammal.

A pharmaceutical composition of the present invention will comprise an effective, non-toxic amount of one or more of the compounds and a pharmaceutically acceptable carrier or diluent. These procedures may involve mixing, granulating, and compressing or dissolving the ingredients as appropriate to the desired preparation.

Thus, if a solid carrier is used, the preparation can be tableted, placed in a hard gelating capsule in powder or pellet form, or in the form of a troche or lozenge. The amount of solid carrier will vary, but preferably will be from about 25 mg to 400 mg. When a liquid carrier is used, the preparation will be in the form of a syrup, emulsion, soft gelating capsule, sterile injectable liquid such as an ampule or nonaqueous liquid suspension. Where the composition is in the form of a capsule, any routine encapsulation is suitable, for example, using the aforementioned carriers in a hard gelatin capsule shell.

A syrup formulation will generally consist of a suspension or solution of the compound in a liquid carrier for example, ethanol, glycerine, or water with a flavoring or coloring agent. An aerosol preparation will consist of a solution or suspension of the compound in a liquid carrier such as water, ethanol or glycerine; whereas in a powder dry aerosol, the preparation may include a wetting agent.

Formulations of the present invention comprise an active ingredient together with one or more acceptable carrier(s) thereof and optionally any other therapeutic ingredient(s). The carrier(s) must be "acceptable" in the sense of being compatible with the other ingredients of Formulation and not deleterious to the recipient thereof.

It will be recognized by one of skill in the art that the form and character of the pharmaceutically acceptable carrier or diluent is dictated by the amount of active ingredient with which it is to be combined, the route of administration, and other well-known variables.

The following examples demonstrate the effect of pirfenidone. and related compounds on:

(1) Murine C57BL/6 peritoneal macrophages (MO) were collected by gavage for in vitro cell culture. These cells were then stimulated by lipopolysaccharide (LPS, *E. coli.*) and/or mannosylated bovine serum albumen (mBSA) to produce and secrete TNF-α to determine the effect of graded concentrations of pirfenidone at the cellular level. The pirfenidone caused a dose-dependent intracellular, as well as culture media, decrease in TNF-α production as measured by ELISA.

(2) In vivo studies (in mice) used intraperitoneal injection of D-galactosamine plus LPS (*E. coli.*) to elicit endotoxin shock and death. When 200 mg/kg of pirfenidone was administered 30 minutes prior to, or within 30 minutes post-injection of the LPS plus D-galactosamine, the shock and deaths were completely prevented. The prevention of shock and death reflects profound inhibition by the expected rise in circulating TNF-α.

(3) In vivo experiments with male mice given injections of LPS (*E. coli.*) and/or mBSA to cause marked elevations of TNF-α in circulating serum demonstrate the ability of injected graded doses of pirfenidone to completely block the elevation of serum TNF-α by these agents.

EXAMPLE I

In vitro, pirfenidone at concentrations of 33–900 micrograms/milliliter inhibited the synthesis and/or release of excessive and pathophysiologic amounts of TNF-α from WEHI 164 cells (Table 1). In vitro, pirfenidone at concentrations of 33 to 300 micrograms/milliliter did not inhibit the killing of WEHI neoplastic fibroblast cells by TNF-α (FIG. 1).

TABLE I

EFFECT OF PIRFENIDONE ON TNF-αINDUCTION
BY MACROPHAGES EXPOSED TO LPS
(Relative TNF-αUnits)

| | | Pirfenidone (micrograms/ml) | | | |
|---|---|---|---|---|---|
| Pre- | 0.0 incubation with pirf. (hours) | 100 | 300 | 900 | Exp # |
| 1 | 0 | >256 | 109 | 105 | 18 |
| 2 | 0 | >256 | 87 | 26 | 7 |
| 3 | 12 | >256 | >256 | 213 | 34 |
| 4 | 12 | 140 | 123 | 103 | 80 |
| 5 | 12 | >256 | 80 | 17 | 7 |
| 6 | 24 | 218 | 209 | 143 | 111 |

Mean +/− S.E. 230 +/− 14 144 +/− 29 84 +/− 31 43 +/− 18

Exposure of thioglycollate-induced murine peritoneal macrophages to LPS in the presence of pirfenidone resulted in a markedly reduced level of TNF-α secreted into the culture medium of these cells. The reduction was directly related to the concentration of pirfenidone in the culture media. No toxicity was apparent with macrophages exposed to 0.9 mg/ml. The greatly reduced levels of TNF-α in the presence of pirfenidone show a statistically significant (P<0.01) inhibition of TNF-α output.

The ability of pirfenidone and related compounds to block the synthesis and the release of TNF-α from macrophages, as well as other cells, was bioassayed by the method of Morgan, Mills, D. L. Lefkowitz, and S. S. Lefkowitz ("An Improved Colorimetric Assay for Tumor Necrosis Factor Using WEHI 154 Cells Cultured on Novel Microtiter Plates," *Jour. Immunol. Method.*, 145:259–262, 1991).

EXAMPLE II

In order to determine the direct impact of graded concentrations of pirfenidone upon the synthesis of TNF-α within the cytoplasm of murine macrophages, cell cultures of macrophages, grown in appropriate culture media, were treated with the respective concentrations pirfenidone for 60 minutes: (1) without exposure to LPS (controls) and (2) exposure to 1.0 pg/ml of LPS (*E. coli.*). Promptly after an exposure for 60 minutes, (a) the macrophages were separated from the culture medium by centrifugation, and (b) the macrophages were lysed. Subsequently, the lysed contents (cell cytoplasm and nucleus) from the macrophage cells were assayed via ELISA for TNF-α levels.

In the controls (no exposure to LPS, *E. coli.*), only very low baseline levels of TNF-α were found within the cytoplasm of the macrophages at the respective pirfenidone concentrations. Even at a concentration of 0.9 mg/ml of pirfenidone, only baseline levels were found. No measurable statistically significant change in production of TNF- occurred (FIG. 5).

In the LPS treated macrophages, the combined cytoplasm and nucleus of cells demonstrated: (1) enhanced synthesis by the cytoplasm of these macrophages of TNF-α in the absence of pirfenidone in the media (FIG. 5), and (2) a pharmacologic inhibition of the LPS (*E. coli.*, 1.0 pg/ml) induced rise in TNF-α synthesis that was directly related to the concentration of pirfenidone in the media (FIG. 5). The pharmacological inhibition of LPS enhanced synthesis of TNF-α within the cytoplasm and nucleus of the macrophages of TNF-α was statistically significant (P<0.01).

EXAMPLE III

FIG. 2A displays the in vitro effect of pirfenidone on macrophages exposed to 0.1 ng of LPS. The highest concentration reduced TNFα from 4500 pg to 1500 pg/ml.

Figure 2B:
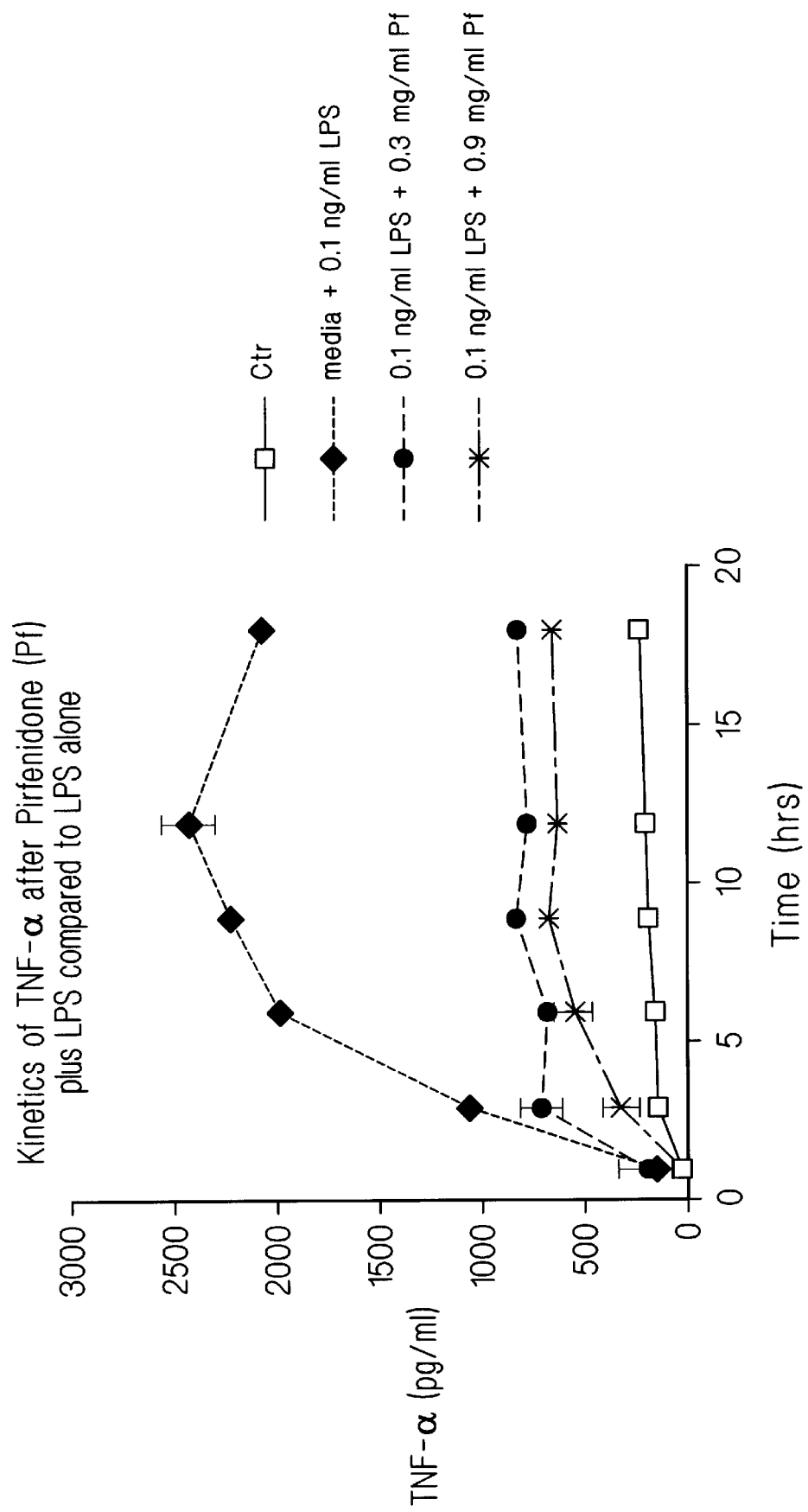
FIG. 2B is a graph showing the kinetics of TNF-α after pirfenidone plus LPS compared to LPS alone.

FIG. 2B shows that the in vitro TNF-α inhibition was dose-dependent, and the marked inhibition was maintained for as much as 18 hours. Maximum reduction of TNF-α synthesis was noted after three hours of incubation as contrasted with controls (not exposed to pirfenidone), where the TNF-α synthesis continued at high levels for up to 18 hours.

EXAMPLE IV

Figure 6:
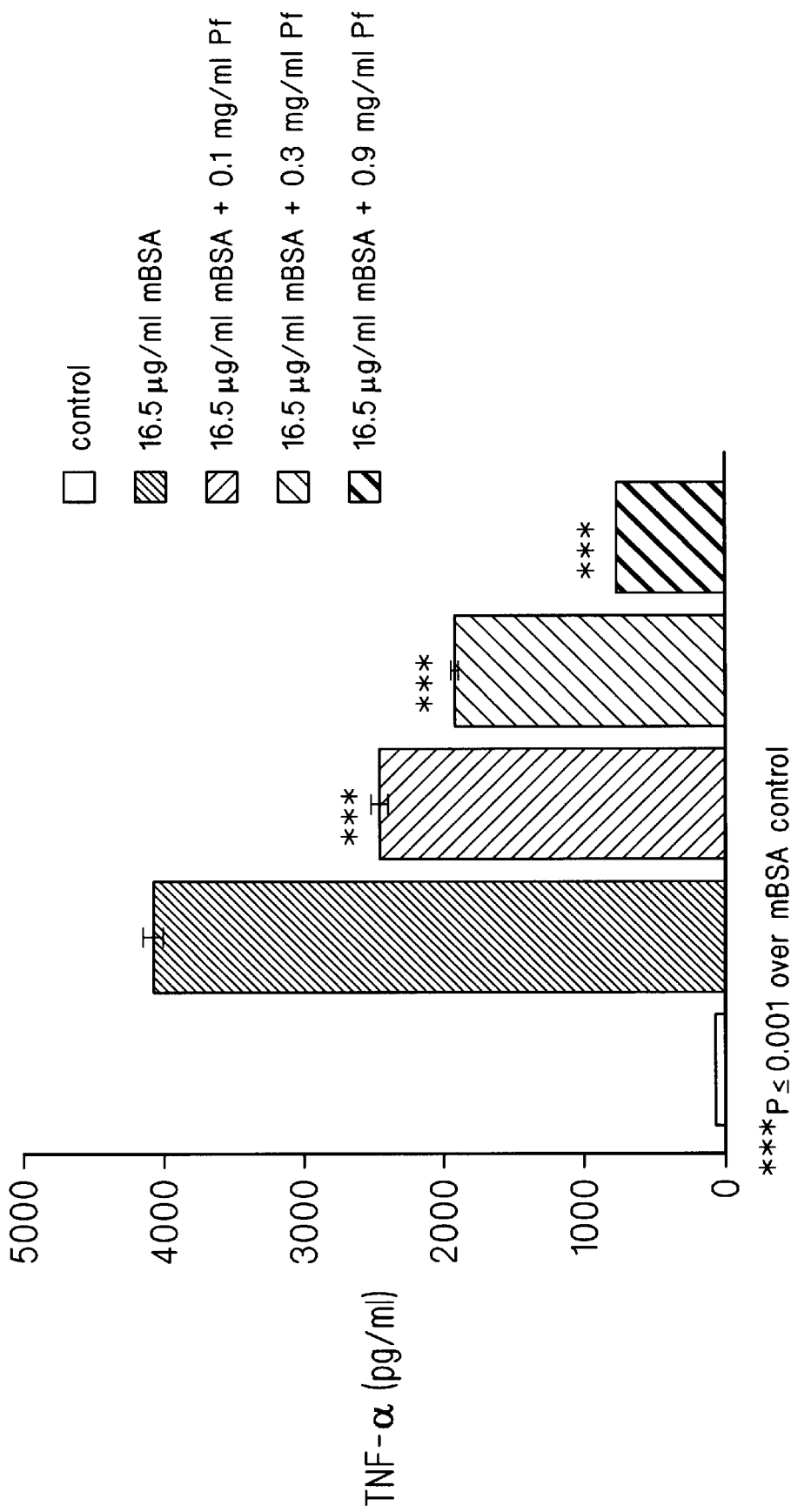
FIG. 6 is a charts showing the inhibition of mBSA induced TNF-α by pirfenidone.

To rule out the possibility that inhibition of TNF-α synthesis by pirfenidone was specific for LPS (*E. coli.*), another enhancer of TNFα synthesis, mannosylated bovine serum albumin (mBSA) was employed. A concentration of 16.5 micrograms/ml induced a sharp rise in TNF-α production. Furthermore, a dose-dependent inhibition of TNF-α production was observed following exposure of the macrophage cells to pirfenidone (FIG. 6).

To ascertain the effects of pirfenidone on TNF-α secretion by cells stimulated with mannosylated bovine serum ablumin (mBSA), thioglycollate peritoneal MO were exposed to 16.5 micrograms/ml mBSA and treated with 0.1 to 0.9 mg/ml pirfenidone. After 6 hours incubation, supernatants were collected and assayed for TNFα by ELISA.

EXAMPLE V

Figure 4:
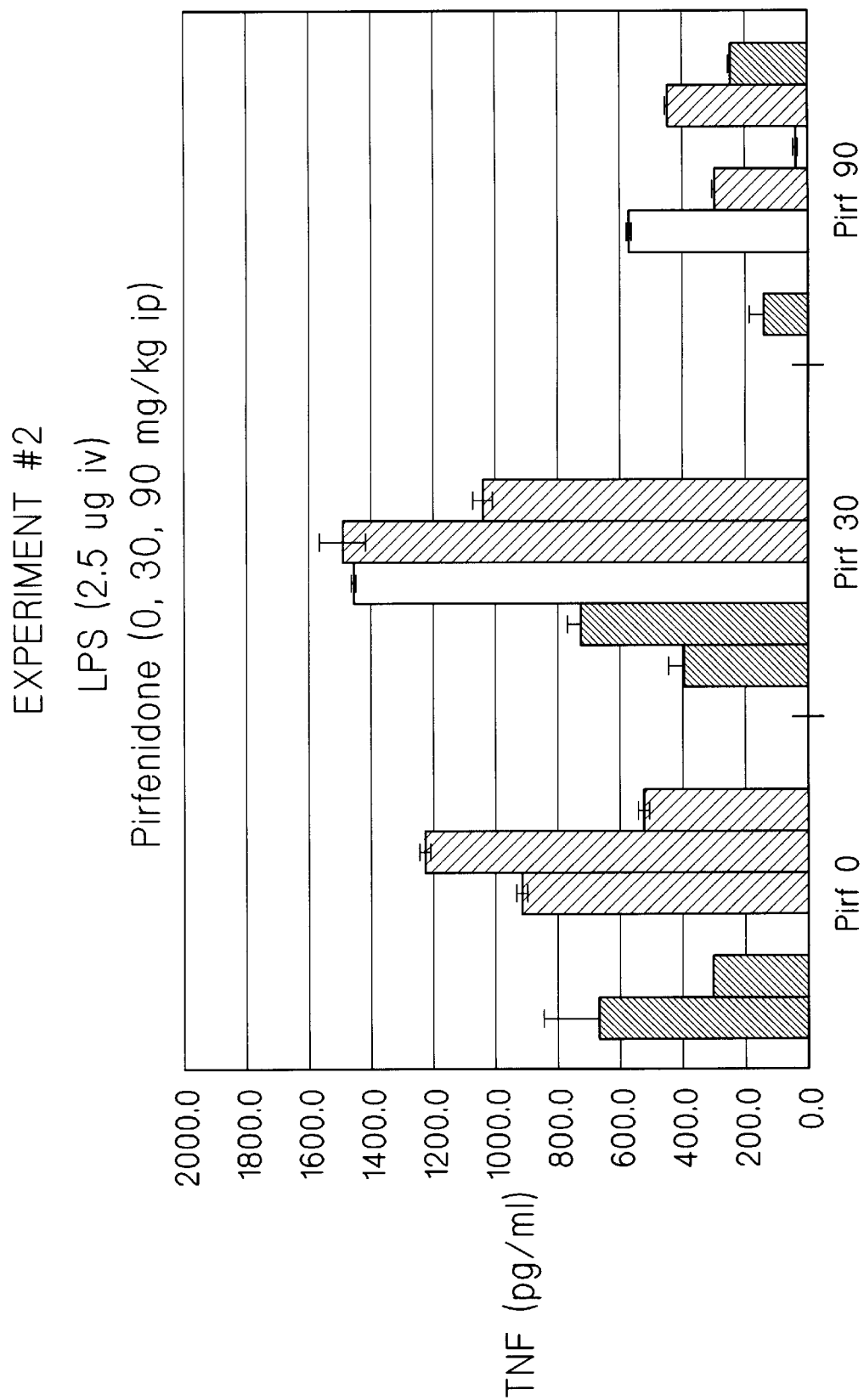
FIG. 4 is a chart showing the inhibition by pirfenidone of the release of TNF-α from cells following stimulation with LPS in intact mice.
Figure 7:
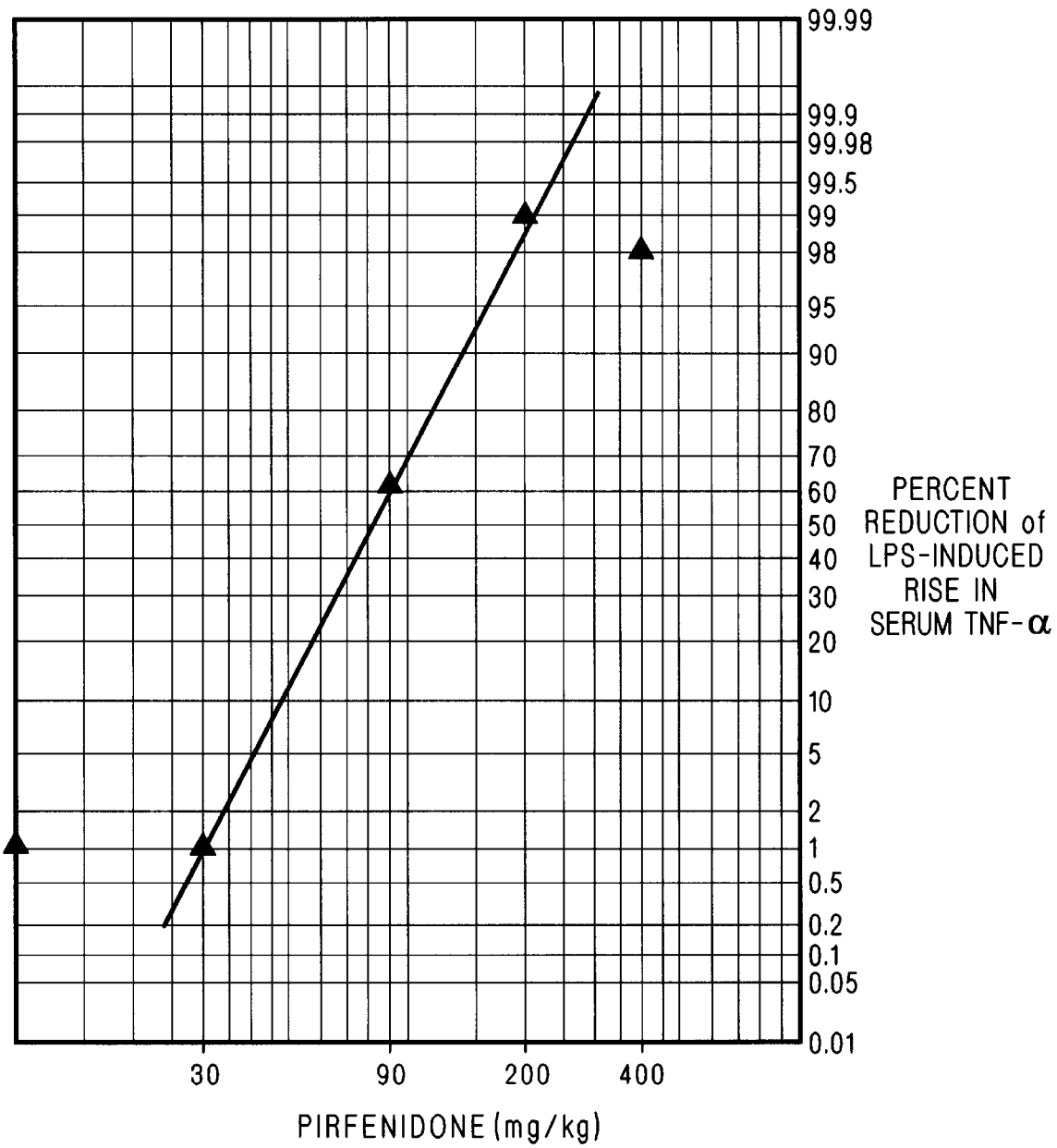
FIG. 7 is a graph of reduction of LPS-induced rise in serum TNF-α as a function of pirfenidone concentration.

In vivo experiments with mice were conducted to measure the circulating serum levels of TNF-α as a measure of the inhibitory action of pirfenidone on TNF-α synthesis and secretion in the intact animal. When the mice were injected i.v. with 2.5 micrograms of LPS (*E. coli.*)/mouse, followed by pirfenidone, i.p., and bled 90 minutes later, a dose-related inhibition of the LPS-induced rise in circulating TNF-α was found (FIGS. 3, 4, and 7). At a dosage of 200 milligrams per kilogram of body weight or greater, complete blockage of the formation and release of TNFα into the circulation of mice was achieved and maintained for many hours. The above experimental models are a modification of that previously described for the in vivo induction of elevated levels of TNF-α in the circulating blood of mice (Haranaka et al., *Cancer Immunol. Immunother.*, 18:87–90, 1984.

EXAMPLE VI

Protection by pirfenidone from LPS (*E. coli.*) shock and death was observed in mice given graded doses of the drug (Table II).

The WEHI bioassays for serum TNF-α levels were confirmed in monitoring tests by using a modification of the basic sandwich ELISA method. All other serum levels of TNF-α were measured entirely by the ELISA method (Winston et al., *Current Protocols in Molecular Biology*, page 11.2.1, Ausubel et al., Ed., 1987).

The LPS was injected intravenously into the mice at a dosage of 2.5 micrograms per mouse, and the pirfenidone was given immediately thereafter. Mice were then bled by cardiac puncture 90 minutes later, and serum samples were then subjected to analysis for TNF-α by an ELISA kit (ENDOGEN).

At a dosage level of 80 mg/kg of body weight, i.p., there was a 50% inhibition of the rise in TNF-α serum levels as compared to the control group (7 mice per group; FIGS. 3 and 7). Pirfenidone also is effective when given orally.

TABLE II

PROTECTION FROM ENDOTOXIN PLUS D-GALACTOSAMINE SHOCK BY PIRFENIDONE (SURVIVAL)

| Pirfenidone (mg/kg) i.p. | Total Number | Number in Shock | Percent Protected |
|---|---|---|---|
| Control | 5 | 5 | 0 |
| 50 | 5 | 4 | 20 |
| 100 | 5 | 4 | 20 |
| 200*** 100 | 5 | 0 | |

Mice were given concomitant 0.5 ml i.p. injections of 600 mg/kg D-galactosamine and 0.005 mg/kg LPS. This was followed immediately by a 1 ml injection of pirfenidone also i.p. Mice were then observed 24 hrs. for the signs of endotoxin shock.
***p ≤ 0.001

EXAMPLE VII

Figure 8:
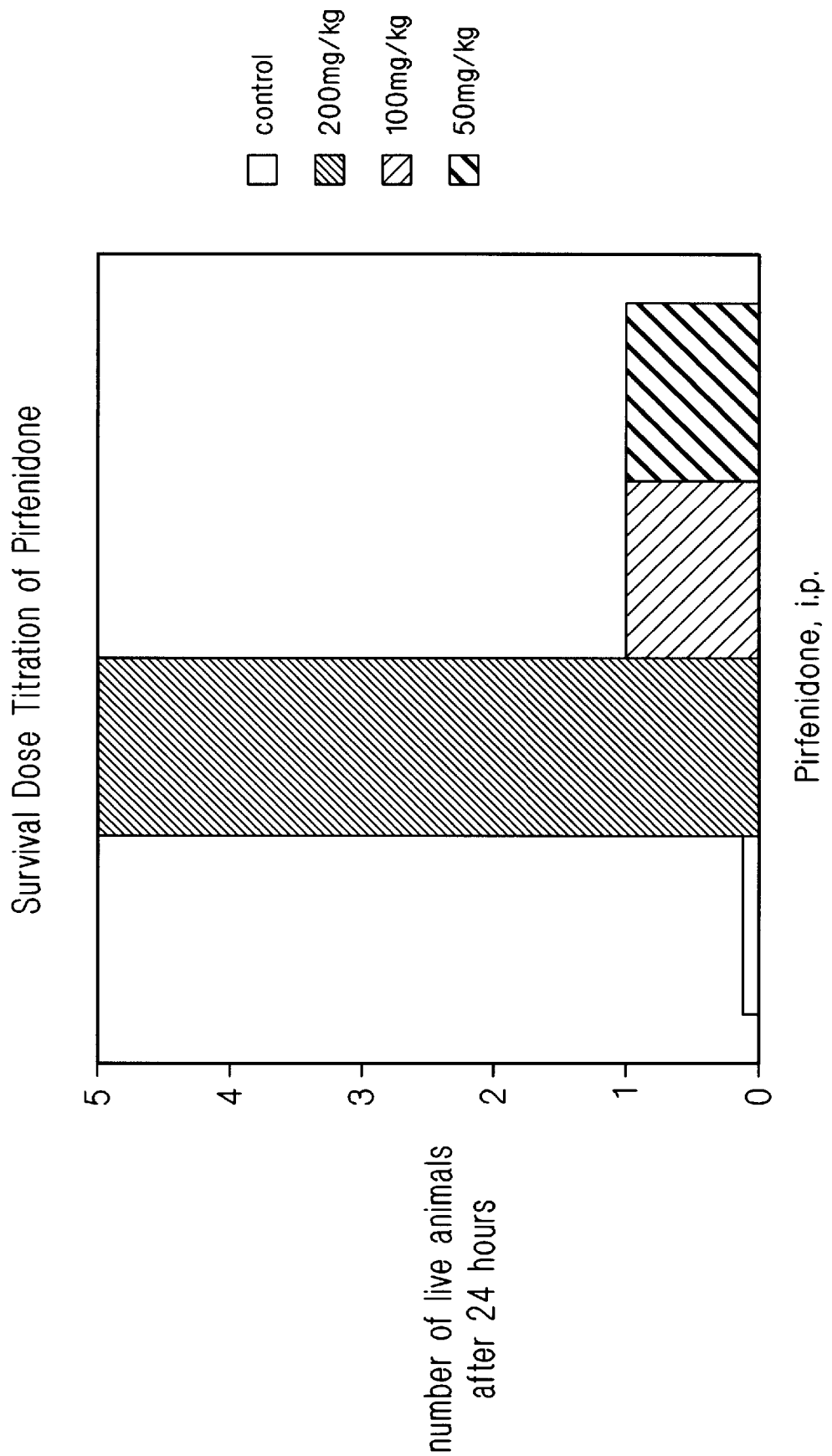
FIG. 8 is a chart showing the survival dose titration of pirfenidone.

In vivo experiments in mice demonstrate the 100.0% shock and mortality caused by a combination of i.v. LPS (*E. coli.*, 50 pg/ml) plus 600 mg/kg of i.p. D-galactosamine. Method: Badger et al., *Circ. Shock*, 44:188–195, 1994). This mortality was distinctly reduced to no mortality by the injection of 200 mg/kg promptly after the injection of the combination of LPS and D-galactosamine (Table III, FIG. 8). The blood serum levels of TNF-α in the surviving pirfenidone-treated mice approached normal baseline levels.

TABLE III

PIRFENIDONE REDUCED ELEVATED MOUSE SERUM LEVELS OF TNF-ALPHA INDUCED BY LPS AND LPS PLUS GALACTOSAMINE

| | (Pirfenidone mg/kg, i.p.) | | | |
|---|---|---|---|---|
| TNF-α Serum Levels | 30 | 90 | 200 | 400 |
| Stimulus | | | | |
| LPS Only 643 +/− 156 pg/ml | 1020 +/− 213 | *247 +/− 77 | *0 +/− 0 | *0 +/− 0 |
| LPS + D-gal 5935 +/− 1893 pg/ml | ND | ND | ***1097 +/− 286 | ND |

Compared to baseline:
*p ≤ 0.05
***p ≤ 0.001
1. Mice were injected i.v. with 2.5 micrograms LPS followed immediately by i.p. injection with either saline or pirfenidone. Mice were exsanguinated at 90 min., sera collected and assayed for TNF-α by ELISA.
2. Mice were injected i.p. with 600 mg/kg D-galactosamine mixed with 0.1 microgram LPS followed immediately by i.p. injection with either saline or pirfenidone. Mice were exsanguinated at 90 min., sera collected and assayed for TNF-α by ELISA.

The in vitro and in vivo experimental laboratory data shown herein demonstrate that the relatively simple non-antigenic heterocyclic compounds of the present invention can inhibit TNFα overproduction and release by mammalian cells. It follows that the compounds of the present invention are useful in inhibiting the overproduction of TNF-α by monocytes, macrophages and other cells in a human. The following two double-blind controlled clinical trials afford strong evidence of the anti-TNF-α efficacy of the present invention.

Strong evidence exists that abnormally high production and release of TNF-α contributes to disease initiation and progression in rheumatoid arthritis (Propert, L., *J. Leukocyte Biol.*, 59:518–525, 1996, pg. 2). Bodner and Foulkes ("Therap. Modulation Cytokines," Eds. B. Henderson and B. Bodner, pp. 221–236, 1996) describe TNF-α mediated pathologies such as rheumatoid arthritis, and the clinical use of TNF-α monoclonal antibodies in the beneficial treatment of this disorder. In addition, several clinical trials using and anti-TNF-α antibody have shown marked clinical benefit, verifying the concept that TNF-α is of major importance in rheumatoid arthritis, Re-treatment clinical studies have also shown benefit in rheumatoid relapses, indicating that the disease remains TNF-α dependent (M. Feldmann, *Annual. Rev. Immunol.*, 14:397–440, 1996).

The results of the following controlled clinical studies emphasize the marked anti-TNF-α action of pirfenidone, since pirfenidone has been shown in many experiments in several laboratories to completely lack (1) antihistaminic activity, (2) andticholinergic activity, (3) immunosuppressive properties, (4) any ability to inhibit cyclooxygenase 1 or 2, and (5) any ability to directly inhibit a specific immunological reaction to an antigen.

EXAMPLE VIII

In humans, preliminary and controlled trials indicate that the effective anti-TNF-α daily oral dosages are in the range of 10 to 25 milligrams per kilogram body weight in divided administration (3 times daily).

IN VIVO DOUBLE-BLIND, OXYPHENBUTAZONE-CONTROLLED STUDY IN RHEUMATOID ARTHRITIS PATIENTS WITH SEVERE DEGENERATIVE ARTHROPATHY

Pirfenidone was studied in 12 patients (35 to 70 years old) with chronic rheumatoid arthritis in a double-blind comparison with 10 patients (35 to 64 years old) treated with oxyphenbutazone. The patients were carefully evaluated and were classed as Stage III disease. Every patient had a history of having been refractory to many NSAID agents. Each patient was assigned to a specific drug group according to a sequence taken from a standard random table. The patients were on the respective drug regimens for 21 days. Improvement compared to baseline was distinctly evident in both groups (50% for oxyphenbutazone, 200 mg t.i.d.; 67% for pirfenidone, 400 mg. t.i.d.).

The clinical findings which showed marked improvement included: (1) morning stiffness and pain, (2) range of motion in affected joints, (3) grip strength, and (4) walking range and time. Although some gastric discomfort was seen with one patient on oxyphenbutazone, and two patients on pirfenidone, no marked side effects were found with either drug during or after treatment. In most patients who benefited, a significant reduction in ESR values occurred.

IN VIVO DOUBLE-BLIND, PLACEBO-CONTROLLED STUDY IN PATIENTS WITH RESISTANT PERENNIAL ALLERGIC RHINITIS AND SINUSITIS

In a double-blind trial with 40 patients diagnosed with resistant perennial allergic rhinitis and sinusitis, the patients were treated with oral pirfenidone, 200 mg q.i.d., for one week, the clinical parameters considered included: (a) nasal patency, (b) nasal secretions, (c) nasal pallor, (d) nasal edema, (e) sneezing, (f) nasal itching, and (g) nasal pain. Statistical analyses of the above parameters for comparing the placebo and pirfenidone groups demonstrated a very significant improvement with pirfenidone with respect to (b) nasal secretions, (c) nasal pallor, (d) nasal edema, (e) sneezing, (f) nasal itching, and (g) nasal pain.

In contrast to pirfenidone treated patients, no significant improvement occurred in (c) nasal pallor, (e) sneezing, or (g) nasal pain. Furthermore, only a much lesser improvement was seen after the placebo with respect to (b) nasal secretions, (d) nasal edema, or (f) nasal itching.

In addition to pirfenidone, the following, closely related compounds, comprising other N-substituted 2(1H)pyridones and N-substituted 3(1H)pyridones have been found or are believed to have efficacy in inhibiting the synthesis and release of TNF-α:

5-Methyl-1-(3-nitrophenyl-2)-(1H)pyridone
5-Methyl-1-(4'-methoxyphenyl)-2-(1H)pyridone
5-Methyl-1-p-tolyl-2-(1H)pyridone
5-Methyl-1-(3'-trifluoromethylphenyl)-2-(1H)pyridone
1-(4'Chlorophenyl)-5-Methyl-2)-(1H)pyridone
5-Methyl-1-(2'-naphthyl)-2-(1H)pyridone
5-Methyl-1-(1'naphthyl)-2-(1H)pyridone
3-Methyl-1-phenyl-2-(1H)pyridone
6-Methyl-1-phenyl-2-(1H)pyridone
3,6-Dimethyl-1-phenyl-2-(1H)pyridone
5-Methyl-1-(2'-Thienyl)-2-(1H)pyridone
1-(2'-Furyl)-5-Methyl-2-(1H)pyridone
5-Methyl-1-(5'-quinolyl)-2-(1H)pyridone
5-Methyl-1-(4'-pyridyl)-2-(1H)pyridone
5-Methyl-1-(3'-pyridyl)-2-(1H)pyridone
5-Methyl-1-(2'-pyridyl)-2-(1H)pyridone
5-Methyl-1-(2'-quinolyl)-2-(1H)pyridone
5-Methyl-1-(4'-quinolyl)-2-(1H)pyridone
5-Methyl-1-(2'-thiazolyl)-2-(1H)pyridone
1-(2'-Imidazolyl )-5-Methyl-2- (1H)pyridone
5-Ethyl-1-phenyl-2-(1H)pyridone
3-Ethyl-1-phenyl-2-(1H)pyridone
1-Phenyl-2-(1H)pyridone
1-(4'-Nitrophenyl)-2-(1H)pyridone
1,3-Diphenyl-2-(1H)pyridone
1-Phenyl-3-(4'-chlorophenyl )-2-(1H)pyridone
1,3-Diphenyl-5-methyl-2-(1H)pyridone
3-(4'-Chlorophenyl)-5-Methyl-1-phenyl-2-(1H)pyridone
5-Methyl-3-phenyl-1-(2'-thienyl)-2-(1H)pyridone
5-Methyl-1-phenyl-3-(1H)pyridone
5-Methyl-1-(4'-methoxyphenyl)-3-(1H)pyridone
5-Methyl-1-p-tolyl-3-(1H)pyridone
1-(4'-Chlorophenyl)-5-methyl-3-(1H)pyridone
5-Methyl-1-(2'-naphthyl)-3-(1H)pyridone
4-Methyl-1-phenyl-3-(1H)pyridone
6-Methyl-1-phenyl-3-(1H)pyridone
5-Methyl-1(2'-Thienyl)-3(1H)pyridone
1-(2'-Furyl)-5-methyl-3-(1H)pyridone
5-Methyl-1-(5'-quinolyl)-3-(1H)pyridone
5-Methyl-1-(3'-pyridyl)-3-(1H)pyridone
5-Methyl-1-(2'-pyridyl)-3-(1H)pyridone
5-Methyl-1-(2'-quinolyl)-3-(1H)pyridone
5-Ethyl-1-phenyl-3-(1H)pyridone
1-Phenyl-3-(1H)pyridone.

The general structure for the 2-(1H)pyridones is:

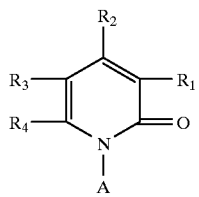

where: R1=alkyl group (CH3, C2H5, etc.); A is phenyl, thienyl, etc., or other aryl group. The alternative is for R3 to be the site of substitution of the alkyl group with R1 remaining as a hydrogen; R2 and R4 are, in every circumstance, hydrogens.

The general structure for the 3-(1H)pyridones is:

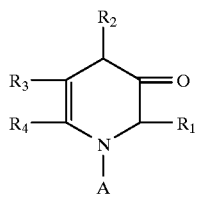

where: R2 or R3=alkyl group or hydrogen, as above; A is phenyl, thienyl, etc., or other aryl group. R1 and R4 are hydrogens.

These compounds can be prepared using methods similar to those set forth in U.S. Pat. No. 3,839,346, issued Oct. 1, 1974, to Gadekar, and titled N-SUBSTITUTED PYRIDONE AND GENERAL METHOD FOR PREPARING PYRIDONES, the disclosure of which is incorporated by reference hereinto. That patent also describes use of some of those compounds in analgesic, anti-inflammatory, and antipyretic treatments. U.S. Pat. No. 3,974,281, issued Aug. 10, 1976; U.S. Pat. No. 4,042,699, issued Aug. 16, 1977; and U.S. Pat. No. 4,051,509, issued Oct. 4, 1978, all to Gadekar, describe further use of pirfenidone in lowering serum uric acid and glucose levels, treating upper respiratory inflammatory conditions, and treating inflammatory skin conditions, in humans and other animals. U.S. Pat. No. 5,310,452, issued May 10, 1994, to Margolin, and titled COMPOSITION AND METHOD FOR REPARATION AND PREVENTION OF FIBROTIC LESIONS, and copending U.S. application Ser. No. 08/243,058, by Margolin, and titled COMPOSITIONS AND METHODS FOR REPARATION AND PREVENTION OF FIBROTIC LESIONS disclose the use of the above compounds in the reparation and prevention of fibrotic lesions.

The compositions of the present invention may be administered in forms consisting of capsules, tablets, powders, granules, syrups, injectable fluids, pills, creams, ointments, inhalable solids or fluids, eye drops, and suppositories.

It will thus be seen that the objects set forth above, among those elucidated in, or made apparent from, the preceding description, are efficiently attained and, since certain changes may be made in the above compositions and methods without departing from the scope of the invention, it is intended that all matter contained in the foregoing disclosure shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A method for the inhibition of the synthesis and release of tumor necrosis factor from various cells, comprising: administering to a human or other mammal an effective dose of one or more pharmaceutical substances selected from the group consisting of N-substituted 2(1H)pyridones, N-substituted 3(1H)pyridones, and pharmaceutically acceptable salts thereof.

2. A method, as defined in claim 1, wherein: the general structural formula of said N-substituted 2-(1)pyridones is:

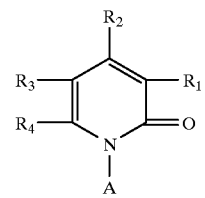

where: R1 is selected from the group consisting of (1) an alkyl group, with R3 hydrogen, and (2) hydrogen, with R3 consisting of an alkyl group; A is an aryl group; and R2 and R4 are hydrogen.

3. A method, as defined in claim 1, wherein: the general structural formula for said N-substituted 3-(1H)pyridones is:

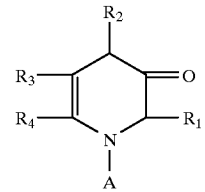

where: R2 is selected from the group consisting of (1) an alkyl group, with R3 hydrogen, and (2) hydrogen, with R3 consisting of an alkyl group; A is an aryl group; and R1 and R4 are hydrogen.

4. A method, as defined in claim 1, wherein: said pharmaceutical substances include one or more compounds selected from the group consisting of:

5-Methyl-1-phenyl-2-(1H)pyridone
5-Methyl-1-(3-nitrophenyl-2)-(1H)pyridone
5-Methyl-1-(4'-methoxyphenyl)-2-(1H)pyridone
5-Methyl-1-p-tolyl-2-(1H)pyridone
5-Methyl-1-(3'-trifluoromethylphenyl)-2-(1H)pyridone
1-(4'Chlorophenyl)-5-Methyl-3)-(1H)pyridone
5-Methyl-1-(2'-naphthyl)-2-(1H)pyridone
5-Methyl-1-(1'naphthyl)-2-(1H)pyridone
3-Methyl-1-phenyl-2-(1H)pyridone
6-Methyl-1-phenyl-2-(1H)pyridone
3,6-Dimethyl-1-phenyl-2-(1H)pyridone
5-Methyl-1-(2'-Thienyl)-2-(1H)pyridone
1-(2'-Furyl)-5-Methyl-2-(1H)pyridone
5-Methyl-1-(5'-quinolyl)-2-(1H)pyridone
5-Methyl-1-(4'-pyridyl)-2-(1H)pyridone
5-Methyl-1-(3'-pyridyl)-2-(1H)pyridone
5-Methyl-1-(2'-pyridyl)-2-(1H)pyridone
5-Methyl-1-(2'-quinolyl)-2-(1H)pyridone
5-Methyl-1-(4'-quinolyl)-2-(1H)pyridone 5-Methyl-1-(2'-thiazolyl)-2-(1H)pyridone
1-(2'-Imidazolyl)-5-Methyl-2-(1H)pyridone
5-Ethyl-1-phenyl-2-(1H)pyridone
3-Ethyl-1-phenyl-2-(2H)pyridone
1-Phenyl-2-(1H)pyridone
1-(4-Nitrophenyl)-2-(1H)pyridone 5-Methyl-3-phenyl-1-(2'-thienyl)-2-(1H)pyridone
5-Methyl-1-phenyl-3-(1H)pyridone
5-Methyl-1-(4'-methoxyphenyl)-3-(1H)pyridone
5-Methyl-1-p-tolyl-3-(1H)pyridone
1-(4'-Chlorophenyl)-5-methyl-3-(1H)pyridone
5-Methyl-1-(2'-naphthyl)-3-(1H)pyridone
4-Methyl-1-phenyl-3-(1H)pyridone
6-Methyl-1-phenyl-3-(1H)pyridone
5-Methyl-1(2'-Thienyl)-3(1H)pyridone
1-(2'-Furyl)-5-methyl-3-(1H)pyridone
5-Methyl-1-(5'-quinolyl)-3-(1H)pyridone
5-Methyl-1-(3'-pyridyl)-3-(1H)pyridone
5-Methyl-1-(2'-pyridyl)-3-(1H)pyridone
5-Methyl-1-(2'-quinolyl)-3-(1H)pyridone
5-Ethyl-1-phenyl-3-(1H)pyridone
1-Phenyl-3-(1H)pyridone.

5. A method, as defined in claim 1, wherein: beneficial effects of said tumor necrosis factor are not inhibited by said pharmaceutical substance.

6. A method, as defined in claim 1, wherein: said pharmaceutical substance is administered to said mammal in a dosage of on the order of about 10 to about 400 milligrams per kilogram of body weight.

7. A method, as defined in claim 1, wherein: said pharmaceutical substance is administered by injection or orally to a human in a daily dosage of from about 10 to about 30 milligrams per kilogram of body weight.

8. A method, as defined in claim 1, wherein: said pharmaceutical substance is administered by injection or orally to a human in a daily dosage of from about 20 to about 25 milligrams per kilogram of body weight.

* * * * *